(12) United States Patent  
Kloepfer et al.

(10) Patent No.: US 7,931,864 B2
(45) Date of Patent: Apr. 26, 2011

(54) METHODS AND APPARATUS FOR ANALYZING AN ANALYSIS FLUID

(76) Inventors: Hans G. Kloepfer, Noblesville, IN (US); Thomas P. Kloepfer, Indianapolis, IN (US); Jason Heim, Indianapolis, IN (US); Reinhard Hafellner, Margarethen (AT)

( * ) Notice: Subject to any disclaimer, the term of this patent is extended or adjusted under 35 U.S.C. 154(b) by 0 days.

(21) Appl. No.: 12/655,589

(22) Filed: Dec. 31, 2009

(65) Prior Publication Data

US 2010/0183477 A1 Jul. 22, 2010

Related U.S. Application Data

(63) Continuation of application No. 10/916,292, filed on Aug. 11, 2004, now Pat. No. 7,695,676.

(51) Int. Cl.
*G01N 33/00* (2006.01)
(52) U.S. Cl. ......................................... 422/68.1; 422/50
(58) Field of Classification Search .................. 422/68.1, 422/50, 58, 55; 435/14, 4; 600/367
See application file for complete search history.

(56) References Cited

U.S. PATENT DOCUMENTS 6,696,240 B1 * 2/2004 Kloepfer et al. .................. 435/4
2003/0109777 A1 * 6/2003 Kloepfer et al. .............. 600/367

* cited by examiner

*Primary Examiner* — Walter D Griffin
*Assistant Examiner* — Christine T Mui
(74) *Attorney, Agent, or Firm* — E. Victor Indiano; Indiano Law Group

(57) ABSTRACT

A meter and test wand system is capable of cooperatively processing an analysis fluid and communicating results to a user. The system includes a meter case including a case front, a case front, a case front, a case bottom, a first case side member, and a second case side member. The first and second case side members connect the case front to case front. The first case side member has a longitudinal dimension between said case front and said case bottom and a latitudinal dimension between said case front and said case front. The first case side member includes a first case ridge; A test wand is capable of receiving an analysis fluid, and includes a cartridge including a cartridge ridge. The cartridge ridge is sized and shaped to matingly engage with said first case ridge to connect said test wand to said meter case.

14 Claims, 19 Drawing Sheets

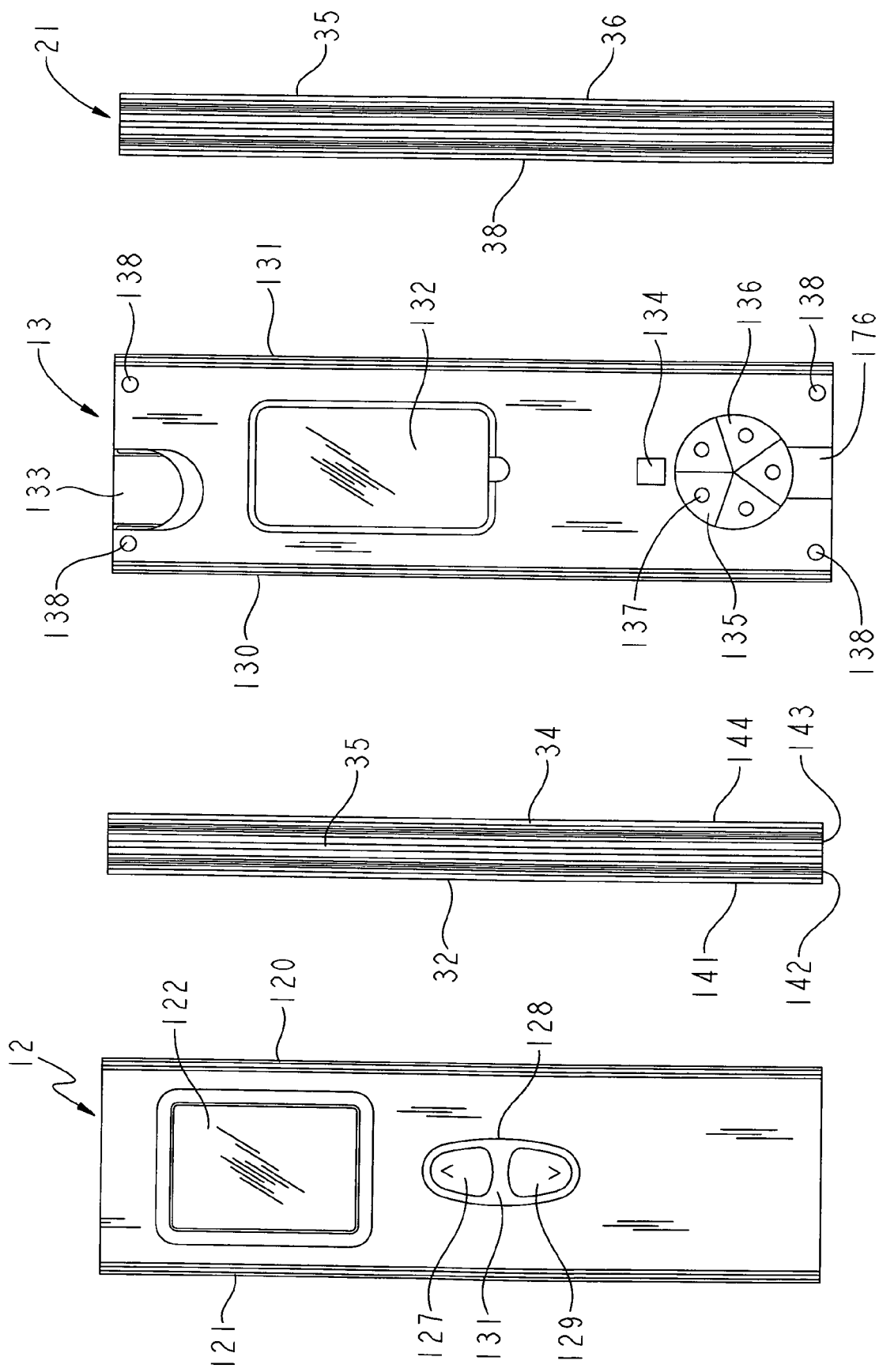

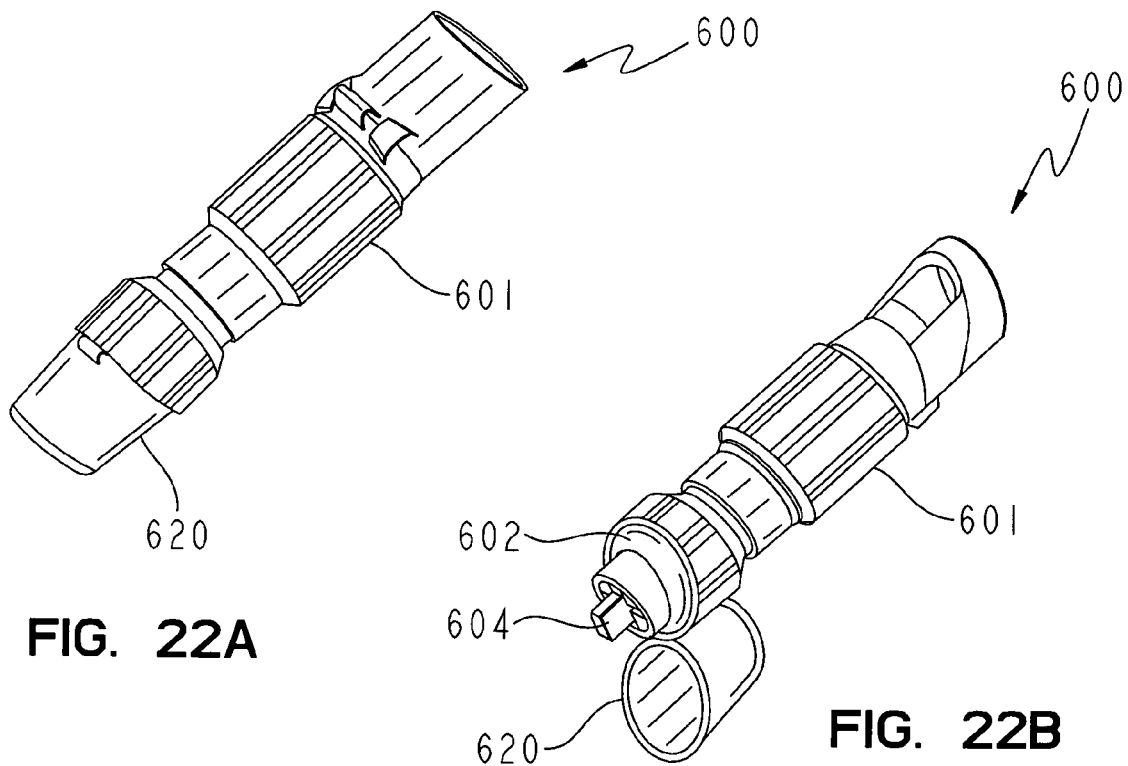
FIG. 22A
FIG. 22B
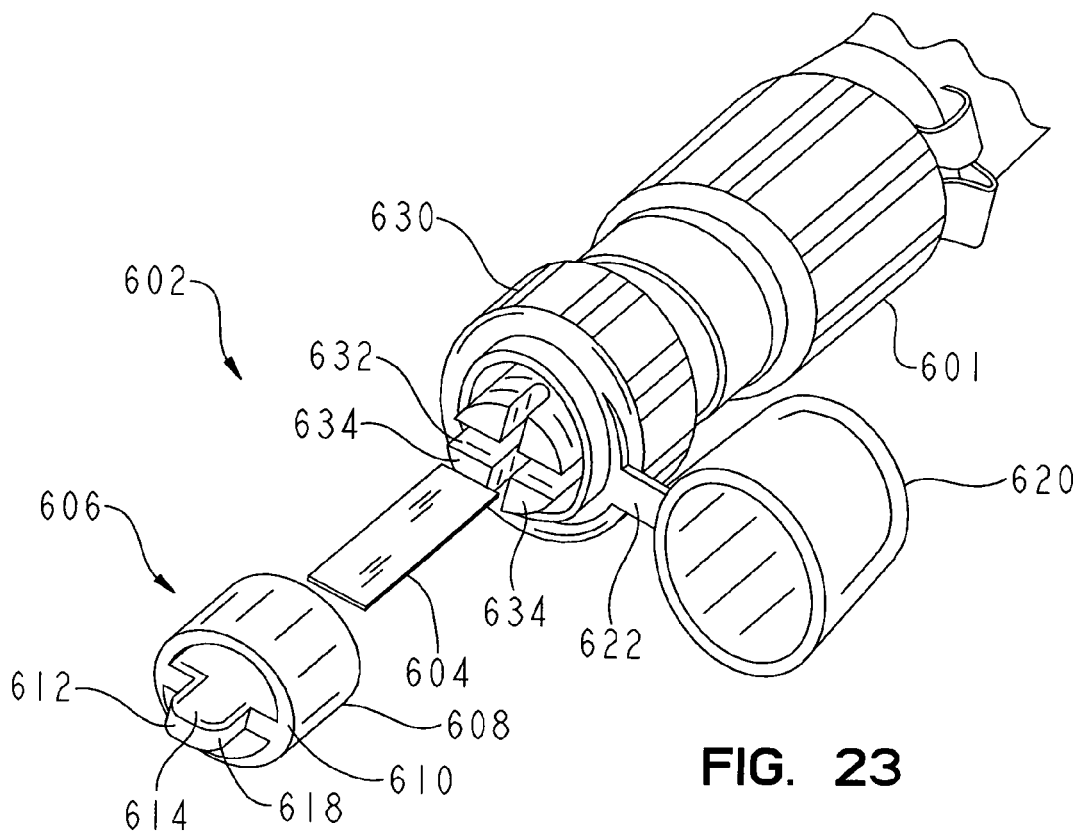
FIG. 23

METHODS AND APPARATUS FOR ANALYZING AN ANALYSIS FLUID

This application is a continuation of Hans G. Kloepfer et al U.S. patent application Ser. No. 10/916,292, which was filed on 11 Aug. 2004 now U.S. Pat. No. 7,695,676, and is fully incorporated herein by reference.

GOVERNMENT INTEREST STATEMENT

This invention was made with Government support under grant number R44 DK059219 from the National Institutes of Health. The Government has certain rights to this invention.

TECHNICAL FIELD OF THE INVENTION

The present invention relates to methods and devices for testing analysis fluids, and more particularly to a consolidated testing apparatus for use in performing analyses of one or more components of a fluid. Significant contemplated applications of the invention are in the biological sciences, especially diagnostic medicine. In this field, analysis fluids would primarily be bodily fluids, notably whole blood.

BACKGROUND OF THE INVENTION

Diabetes has been referred to as the "undiagnosed epidemic of the third millennium". Some experts predict the number of diabetics world-wide to triple over the next 15 years to about 320 million. Self-monitoring of blood glucose (SMBG) is considered the quintessential prerequisite for diabetes management and treatment. As will be explained in more detail, most current SMBG systems, whether designed for patient or professional use, still have significant limitations.

The three major types of diabetes are type 1 (formerly insulin-dependent diabetes mellitus, IDDM, juvenile-onset), type 2 (formerly non-insulin-dependent diabetes mellitus, NIDDM, adult-onset), and gestational diabetes. About 130,000 children in the US have type 1 diabetes. Treatment for type 1 consists of insulin injections, diet and exercise.

In type 2 diabetes, treatment may include insulin, but preferably oral glucose lowering agents, diet, weight reduction and exercise. Approximately ninety percent (90%) of diabetics are type 2.

Diabetics are predisposed to heart disease, peripheral vascular disease, stroke, retinopathy, kidney disease and neuropathy. The latter is associated with amputations, silent myocardial infarction and sudden death, and it accounts for over 300,000 hospitalizations in the United States each year. Today's total diabetes-related toll to the US economy (direct and indirect costs combined) is estimated to approach $150 billion.

As a true cure for diabetes remains elusive, tight glucose control will continue to be the sine-qua-non of diabetes combat strategies. The benefits of tight glucose control in curbing diabetes-related complications are now authoritatively documented. This evidence also suggests that a large portion of type 2 diabetics may benefit from tight glucose control and insulin. As worldwide knowledge about diabetes will be nurtured by the information age and media-assisted education, masses of undiagnosed diabetics who would benefit from tight glucose control will eventually be brought into the system. Since testing technology will also further mature, these megatrends will co-functionally establish an enormous market for SMBG in the future.

The mainstay of treatment for type 1 and many type 2 diabetics is SMBG in conceit with responding self-administration of insulin to harmonize glucose levels. Current SMBG systems are typically comprised of a test strip-type, dry chemistry device. The test strip is insertable into a hand-held meter that contains a display that gives the user a read-out of results. Alternately, results can be obtained by comparing reaction colors to printed color charts.

From a provider perspective, the main shortfall is that current systems are generally limited to the measurement of glucose. This is in drastic discord with the concept of diabetes as a multi-factorial metabolic syndrome. From a user point of view, there are still limitations in those features that consumers and users believe to be important, such as (1) minimal invasiveness; (2) speed of analysis and (3) ease of performance and minimal complexity (inconvenience) from primary and auxiliary product mixes.

The majority of presently marketed SMBG systems utilize more or less 'invasive' technology (lancing of fingertips) to obtain blood samples in a range between 2 and 30 μL. Non-invasive and minimally invasive technologies have been under active development for years, but made it to market only on a very limited scale due to technical difficulties.

Invasive Systems. Several dry-chemistry technologies exist for testing of whole blood specimens. In most devices, liquid reagents are applied onto solid support substrates by some impregnation or coating method. After solvent evaporation, the dry and therefore stable reagent is contained within a reactive zone or signal member (test field). As the blood sample makes contact with the reagents, a chemical reaction is initiated between analyte in the blood and the reagents on the test field. In most conventional test strips the analyst provides blood to test fields manually, contacting the strip with a drop or unspecified portion of a drop of blood. This technique has limitations with respect to constancy of volume applied and locations on the test field surface contacted by the drop. Consequences can be under- or over-sampling, or heterogeneous distribution of blood and hence reaction signal.

Both photometric and electro-sensimetric detection principles are in use. The vast majority of systems used to employ reflectance photometry, however, in recent years an increasing trend towards electrochemical detection ('sensors') has occurred.

In meters that measure reflectance photometry, light of a wavelength absorbed by the colored reaction product is shined onto the surface of the test field and the reflected portion is monitored. In contrast to conventional photometry where absorbance is measured from reduced light transmittance in the direction of the incident beam, reflectance is measured at locations angled away from incident light. As light of varying wavelengths is reflected in different directions, an informed choice must be made as to which incident and reflective angles to select for obtaining a signal that is most sensitively and most specifically related to concentration. Preferably, the photocurrent detector (photodiode) of the metering device is positioned at a location where unspecific scattering is minimal and specific reflectance maximal. However, since the two can usually not be completely spatially separated, pure signals are by definition unobtainable ('needle in a haystack' phenomenon). This is one reason why it is so difficult to achieve universal standardization of these systems and why the systems differ so much among each other, resulting in widely scattered method means in proficiency testing surveys.

Another limitation resides in the method by which cellular component of blood is separated from plasma. In older products, plasma was separated by soak through methods into coated bibulous materials or reagent films. Cells were then manually removed from the site of blood application by either washing or wiping, potentially giving rise to significant operator-induced errors. Several newer methods permit separation by means other than washing or wiping. The most frequently used are separation by porous glass fiber fleeces or membranes. In these matrices, pore sizes are chosen so that cellular component is held back within the matrix, whereas plasma diffuses through the separating and into the detection layer.

In most colorimetric test strips the separating layer is sandwiched against the detection layer. The reflectance measurement is then made at the side of the test strip opposite to the side of blood application. To keep needed blood volume low, the thickness of the separation layer is kept at a minimum. An adverse consequence is that spatial separation of red cells from the site of measurement is then so small that the thin zone of separation material that is devoid of cells incompletely shields cells. In instrumented measurements this 'shining through' effect of red cells can, as long as the effect is constant, be corrected by calibration or a dual wavelength measurement. However, such corrective methodology makes measurements more complex and less precise.

The shining through effect of red cells is particularly disadvantageous for visual interpretation. It is for this reason that most present-day colorimetric test strips cannot be read visually. Visual interpretation can serve as a confidence check for quantitative results provided by the meter. And in locations where meters are not readily available (rural areas, doctors office, ambulance, third world) concentrations can still be determined semi-quantitatively by visual comparison of reaction colors to standardized color charts. Unfortunately, the feature of visual backup is realized only in a minority of present-day systems.

Non-Invasive (NI) and Semi-Invasive Technology. The goal for the SMBG market, a completely non-invasive glucose monitoring technology, although pursued for over a decade, has so far proven elusive, despite perennial promises from companies in the industry. These failures have led to predictions that completely non-invasive optical technology (infrared or other) may not make it to market in any significant way, for both cost and technical reasons. It is also argued that this lack of success was predictable from early theoretical considerations of signal engineering. These considerations include the numerous and variable challenges of isolating a meaningful signal against a background of overpowering non-specific noise, such as noise from water. An authoritative recent review of NI glucose testing technology concludes that: "... none of the NI experiments reviewed provides proof that the signal is related to actual blood glucose concentration. Clark error grid presentation shows performance that is not acceptable for home glucose meters."

A promising alternative to non-invasive is "semi-invasive" or minimally invasive testing using interstitial fluid (IF). The only product currently marketed that employs this technology is Glucowatch™ from Cygnus, Inc. It uses electrically stimulated (reverse iontophoresis) glucose extraction from IF into a sensor-equipped sample pad. The product was recently approved by the FDA but only for supplementary (trend) testing. Reported problems with IF sampling are variations in skin thickness and permeability, changes in blood/IF equilibration, sweating, signal instability and skin irritation. Furthermore, the watch must be recalibrated every 12 hours which is done by invasive finger stick measurements.

Several more recent devices employ electrochemical (sensimetric) detection. Good progress in system miniaturization has been achieved with these methods because they can function on whole blood, obviating the need for a plasma-consuming, cell-separating member. In some of these products miniaturization is further aided by provision of capillary sampling techniques. Despite these improvements, a major limitation of sensor methods is that visual backup is completely lost. This places a very heavy burden on the manufacturer as even minor flaws in test strip architecture or signal conductivity could have disastrous consequences. Hematocrit dependence in sensor methods can also be substantial due to 'dilution' of the electrochemical reaction milieu by cellular component. Furthermore, in these devices signal output is, as in the case of reflectance measurement, non-linear with respect to concentration, requiring complex mathematics for calibration. Finally, the technical sophistication and manufacturing complexity of the sensor methods makes it difficult to produce them at low cost.

In the future the SMBG market will increasingly be driven by consumer demand, managed care, and cost pressures from third party reimbursement companies. In this environment a market conversion from established and affordable invasive whole blood technology to unproven and costly non-invasive systems appears unlikely. However, it is expected that the market will migrate to invasive systems which minimize invasiveness and its associated pain. As such, the Applicant's minimally invasive and relatively less painful technology is believed by Applicants to better achieve the goals sought by the industry, and be well placed in the direction in which the market is heading.

SUMMARY OF THE INVENTION

The present invention comprises a hand-held meter that works cooperatively with a test wand to process an analysis fluid using the chemistry on test strips contained in the test wand. The capillary flow technology of the present invention enables the removal of obstructions in the analysis fluid that interfere with optical measurement of characteristics of the analysis fluid. Optical measurements include, but are not limited to, transmittance, reflectance, luminescence and fluorescence measurements. In the preferred embodiment, the capillary flow enables transmittance measurement through clear reactive films.

Embodiments of the present invention enable miniaturization of a blood sample volume to less than 300 nanoliters by a thin film, capillary flow micro-fluidic technology. Embodiments of the present invention also enable monitoring of reaction signals by rehydration by blood plasma of transparent polymeric reagent films, using a transmittance-recording, handheld meter. In co-functionality with the meter, the testing consolidation technology can integrate into one single disposable test wand: (1) lancing site preparation, (2) lancing, (3) sampling and dosing, (4) plasma acquisition by rehydrating dry film, (5) cell and excess blood removal exclusively achieved by capillary force, and (6) instrumented and/or visual signal monitoring.

The embodiments can be operationally rugged and extremely user friendly. Intrinsic qualities of the embodiments can include: (1) quantitative measurement by transmittance photometry with visual backup, (2) incorporation of all testing parts and steps into a single unit, eliminating product clutter and making testing easier, (3) virtually painless testing due to the ultra-miniaturization of lancing procedure and sample size, and the potential for alternate site (non-finger-stick) sampling, and (4) environmentally independent and safe testing and disposal due to lancet, test strip and antiseptic swab enclosure before and after use.

Although the dynamic range of transmittance and reflectance measurement is in theory similar, use of a transmittance system in conjunction with a non-scattering chemistry matrix offers the advantage of increased signal strength and allows use of a smaller chemistry matrix. The increased signal strength and quality provides for reduced energy consumption (longer battery life) and better transient performance of the light source, usually a light emitting diode (LED). The smaller chemistry matrix enables a smaller sample volume, an extremely attractive feature in many point-of-care (POC) applications.

Measuring transmittance through a non-scattering chemistry matrix offers distinct advantages over reflectance or electrochemical measurement. One advantage is that the surface area of the chemistry matrix can be kept minimal. By contrast, in highly scattering media the reflected light is laterally dispersed as quantified by the point spread function which strongly depends upon the scattering characteristics of the chemistry matrix. This 'blooming' effect requires the light source to illuminate an area well inside the boundary of the active chemistry matrix. For example, to account for manufacturing tolerances, a 3 mm diameter light spot would typically require a 6 mm diameter chemistry pad. When measuring transmittance through a non-scattering media, light absorption is locally focused and the chemistry matrix could be as small as 3 mm when using a 2 mm diameter light spot. This reduction from a 6 mm to a 3 mm diameter reduces test field surface and blood volume needed by a factor of four.

A second advantage is that the transmittance measurement is simpler than the reflectance measurement. For a reflectance measurement, the overwhelmingly dominant signal in the detection region is specular reflection from the surface of the analyte pad. This specular reflection is typically devoid of specific analyte-related information, thus greatly enhancing background noise while simultaneously diminishing useful signal information contained in the remaining diffusely scattered component of the reflection. In contrast, because of a much better S/N ratio, transmittance measurement enables faster signal integration, thus requiring less time for obtaining high precision results.

A third advantage is that transmittance measurement decreases the need for high precision electronics and shielding. High precision electronics and shielding add to the cost of the measurement system as well as the power requirements.

A fourth advantage is that a transmittance meter is easier to calibrate than a reflectance meter because: a) a transmittance measurement has a linear signal-to-mass relationship, and b) it is much more straightforward and easier to implement a matchup of the chosen LED emission range with reactant absorbance maxima. For both transmittance and reflectance, the usual route to instrument accuracy is calibration using a calibration standard measurement made contemporaneously with the analyte measurement in order to scale the source output. For the reflectance measurement, geometry demands that a known, stable calibration target must be presented to the optics for each measurement. This typically requires an onboard calibration target cleverly configured to remain clean while still being easily optically available; or alternatively the undosed teststrip can be presented as a calibration target. For the transmittance measurement the calibration can be performed by a simple measurement with nothing inserted in the optical path. Thus the transmittance measurement does not require a calibration target.

An advantage of a transmittance over an electrochemical sensimetric measurement is that a visual backup optical indicator (color comparison chart) can be provided that allows immediate check of extreme (and possibly aberrant) readings in what could be an emergency situation.

In comparison to the current state-of-the-art, the embodiments of the present invention can include several novel features, including the following: (1) because cells do not adhere to 'film' when blood is pulled through the capillary channel, the need for a discrete plasma separating member (cell filter) can be eliminated; (2) owing to laminar flow of blood over 'film', the need for a blood spreading layer, as required in many other current test strips, can be eliminated (Together, these two features enable ultra-miniaturization, making the method minimally invasive and virtually pain-free.); (3) since cellular component and excess blood is continually removed from 'film', cells are inhibited from clogging or temporarily covering the test field surface (This 'mobile sample' feature renders the device essentially independent from interference by hematocrit.); (4) linear optical signals can be acquired from transmittance measurement; in contrast, all present instrumented colorimetric test strips monitor reflectance, relying on a standard curve that is (a) non-linear at all concentrations, and (b) based on an inverse and complicated (Kubelka-Munk) relationship between concentration and reflectance (The capacity for linear measurement simplifies product development and meter calibration.); (5) visual backup or visual monitoring, which is especially important in environments with limited infrastructure and resources (cost or unavailability of meters, batteries, etc.), but also appreciated by those who prefer visual backup to confirm the test results displayed by an electronic device; and (6) incorporation of all operational elements into a single disposable consolidated test wand (which has never before been accomplished), makes testing extremely easy, fast, and thus highly accessible.

The user visually observes sampling and discontinues it when the transparent reaction capillary window is filled with blood. Inaccurate sampling is a lingering problem with current SMBG products. Over-sampling is particularly hazardous as it can lead to life threatening insulin over-administration in response to an erroneously high glucose reading. In the present invention, over-sampling will not result in an erroneous test result.

The features of the present invention can allow the user a high level of control over the analytical process. Transparence of the test strip cover panel allows visual observation of complete dosing through the circular opening in the front end of the test wand. After testing, complete removal of blood can be ascertained in the same fashion. Reaction signals can also be visually confirmed. (With sensor methods, the user has to completely rely on built-in, 'black box' QC features).

Beyond these features, the intrinsic capacity of the technology to permit separation of nanoliter quantities of blood plasma or other analysis fluids from cellular or other particulate suspensions has universal applicability to the complex analytical systems encountered today in biomedical science.

Another feature of the present invention is the ability to connect test wands to the sides of the meter. This feature enables a user to attach the desired number of test wands necessary for a period of time to the meter, and put the meter with attached test wands in a pocket, purse or other carrier. This eliminates the need for a pouch to hold all of the test utensils. Then as the user uses a test wand, they can dispose of the test wand and not have to carry unneeded components around. A method is disclosed that allows multiple test wands to be attached longitudinally and latitudinally along the sides of the meter.

Another important feature of the present invention is the design of the test wand to easily cooperate with a meter to process an analysis fluid, and the methods for processing an analysis fluid. The test wand includes a test wand holder and a test strip. The test strip contains a reagent and at least one layer that has arms that extend out a slot in the test strip holder. The analysis fluid is placed at the distal end of the test strip. When the test wand is inserted into the test wand opening of a meter, the side wall of the test wand opening engages the arm of the test strip, pulling the test strip in the proximal direction, causing the analysis fluid to flow in the proximal direction to expose a portion of the reagent on the test strip that has reacted with the analysis fluid. The exposed reagent can then be analyzed by the meter. Several methods and associated apparatus are disclosed, including a panel separation method in which the layers of the test strip are separated to cause a capillary force to expose a portion of the reagent; a panel sheer method in which the layers of the test strip are slid relative to one another to cause a capillary force to expose a portion of the reagent; and a wiper method in which a wiper wipes the analysis fluid from a portion of the test strip to expose a portion of the reagent.

These and other features of the present invention will become more apparent to those skilled in the art in connection with a review of the drawings and detailed description of the invention set forth below.

BRIEF DESCRIPTION OF THE DRAWINGS

FIGS. 2 A-D are views of the front, right, back and left sides of the meter case, respectively;

FIGS. 22 A-B are views of an alternative embodiment of the consolidated test wand that does not require a cartridge;

FIG. 23 is an exploded view of the alternative embodiment of the consolidated test wand shown in FIGS. 22 A-B;

DETAILED DESCRIPTION OF THE INVENTION

Figure 1:
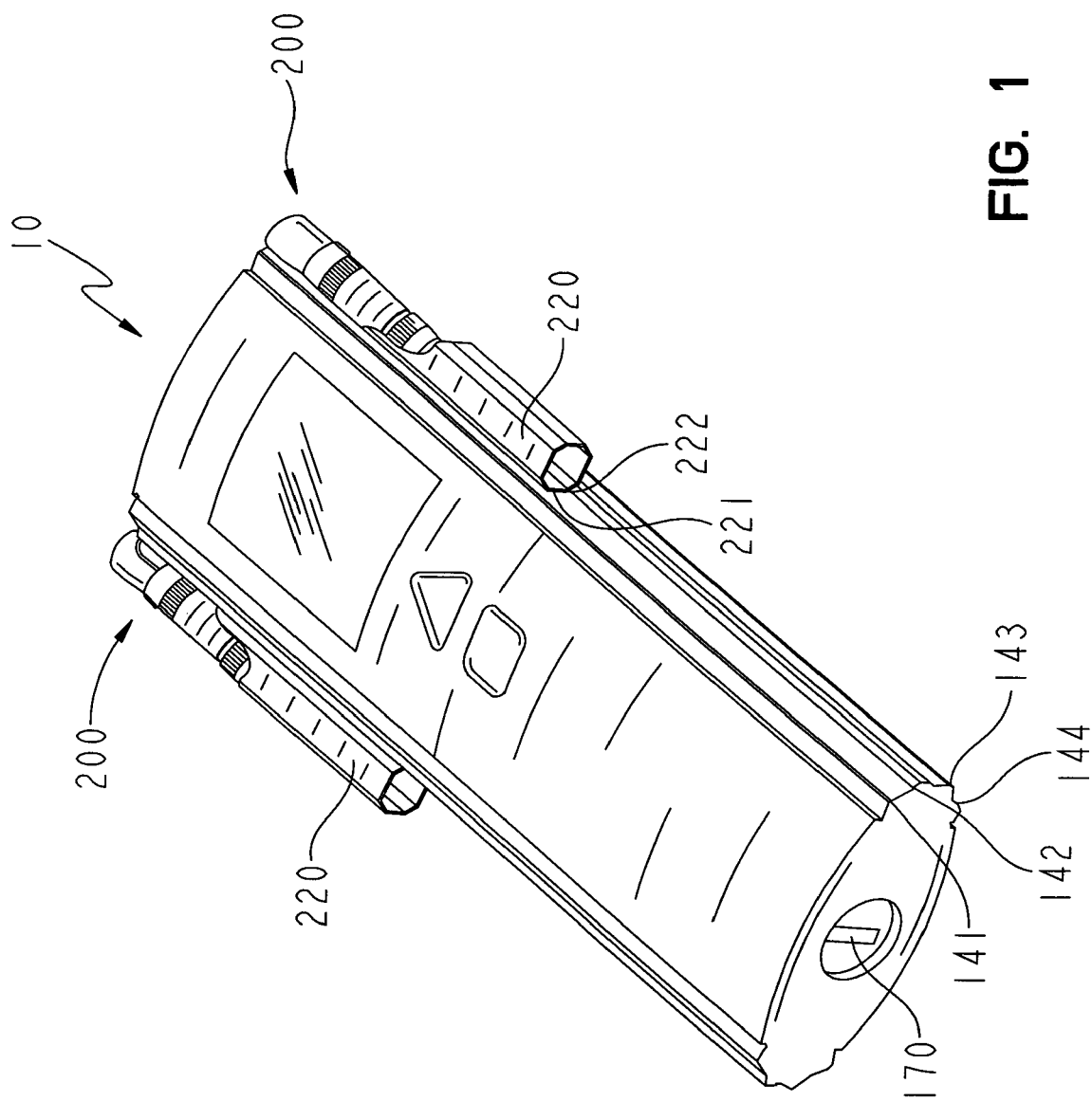
FIG. 1 is a perspective view of the meter 10 with consolidated test wands 200 attached.

FIG. 1 shows a meter 10 and a first and a second consolidated test wand 200 of the present invention. The consolidated test wand 200 is used to obtain a blood sample, and the meter 10 is used to analyze the blood sample and provide feedback regarding the blood sample. The meter 10 and the consolidated test wand 200 are cooperatively designed such that multiple consolidated test wands 200 can be attached to the meter 10 for easier carrying by the user, and such that a blood sample collected with the test wand 200 can be processed properly by the meter 10 through the interaction of the various features of the meter 10 and the consolidated test wand 200 as described hereinafter.

The casing of the meter 10, best shown in FIGS. 2A-2D and 3A-3C, includes a case front 12, a case back 13, a case top 16, a case bottom 17, a right case side member 20 and a left case side member 21. The case front 12 includes a right front lip 120 that extends along the perimeter of the right side of the case front 12, and a left front lip 121 that extends along the perimeter of the left side of the case front 12. The case back 13 includes a right rear lip 130 that extends along the perimeter of the right side of the case back 13, and a left rear lip 131 that extends along the perimeter of the left side of the case back 13. The right case side member 20 includes a front channel 32 sized and shaped to matingly join with the right front lip 120 of the case front 12, and a rear channel 34 sized and shaped to matingly join with the right rear lip 130 of the case back 13. The left case side member 21 includes a front channel 36 sized and shaped to matingly join with the left front lip 121 of the case front 12, and a rear channel 38 sized and shaped to matingly join with the left rear lip 131 of the case back 13. In the preferred embodiment, the case front 12 and the case back 13 are joined by sliding the front and rear channels 32, 34 of the right case side member 20 over the right front lip 120 of the case front 12 and right rear lip 130 of the case back 13, respectively, and by sliding the front and rear channels 36, 38 of the left case side member 21 over the left front lip 121 of the case front 12 and left rear lip 131 of the case back 13, respectively.

Figure 3A:
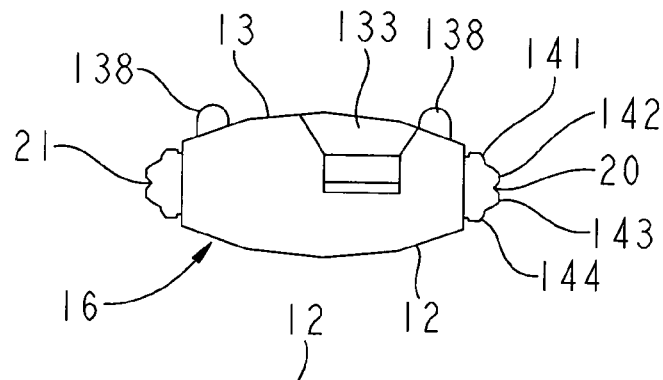
FIGS. 3 A-C are views of the top, front and bottom sides of the meter case, respectively.
Figure 3B:
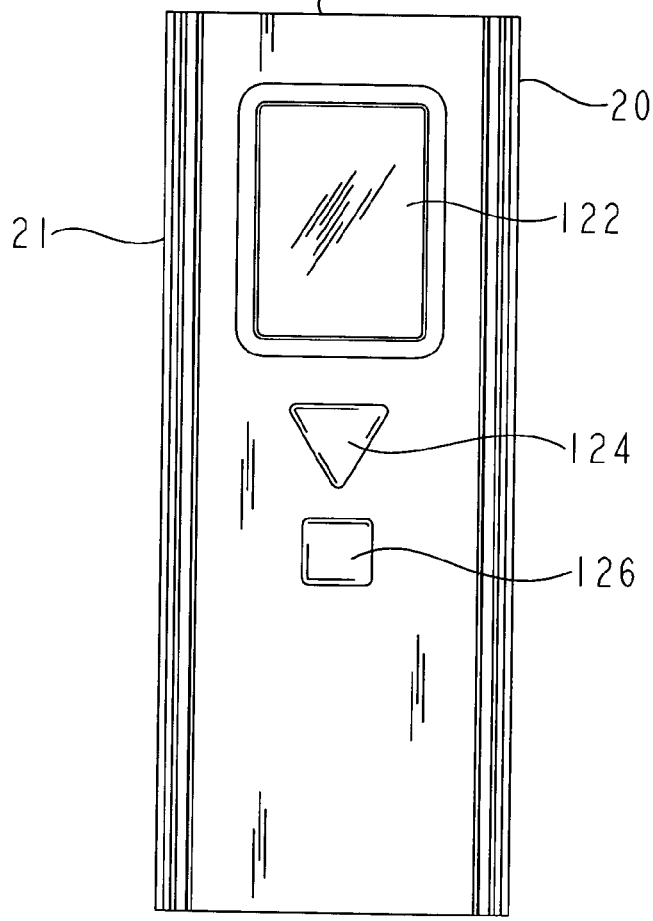

The meter 10 also includes a display 122 for the display of information, and one or more buttons to control the meter 10 and the display of information on the display 122. FIG. 3B shows one embodiment of the meter 10 with two buttons, an upper triangular button 124 to scroll through information displayed on the display 122, and a lower square button 126 to select displayed information for the control of meter functions. FIG. 2A shows a second embodiment of the meter 10 with an elongated toggle button 128 to control meter functions. The toggle button 128 includes an upper portion 127 and a lower portion 129 to scroll up or down, respectively, through the information displayed on the display 122, and a central portion 125 that can be depressed to select the desired item displayed on the display 122.

The case back 13, best shown in FIG. 2C, includes a battery cover 132, a code chip slot 133, a light pipe opening 134, a color chart 136, a visual back-up test wand opening 176, and rubber feet 138. The battery cover 132 is removable to replace the batteries that power the meter 10. In the embodiment shown, two AAA batteries are used, however, other size batteries could be used depending on the power and size considerations for the meter. The code chip slot 133 is configured to accept a code chip containing information on the test strips to be used with the meter 10. The code chip may include information regarding the meter or the test strips; for example the code chip could include lot specific calibration information for the lot of test strips currently being used with the meter. The light pipe opening 134, the color chart 136, and the visual back-up test wand opening 176 are all part of the visual back up feature provided by the meter 10 which is explained later in this section. The rubber feet 138 form a platform to help protect the meter 10 and its various features from damage, and to reduce sliding of the meter 10 during use.

Figure 3C:
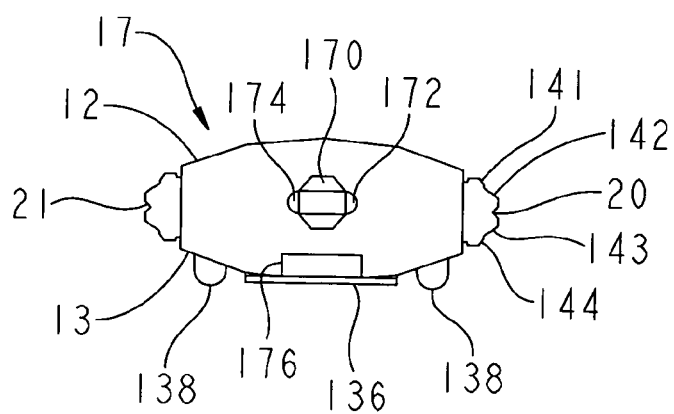
Figure 4B:
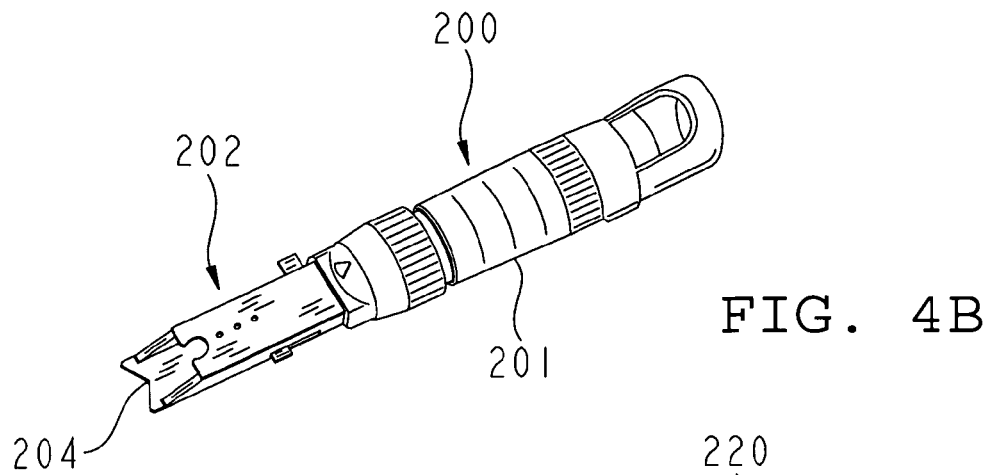
FIGS. 4 A-C are views of the consolidated test wand and cartridge.
Figure 4C:
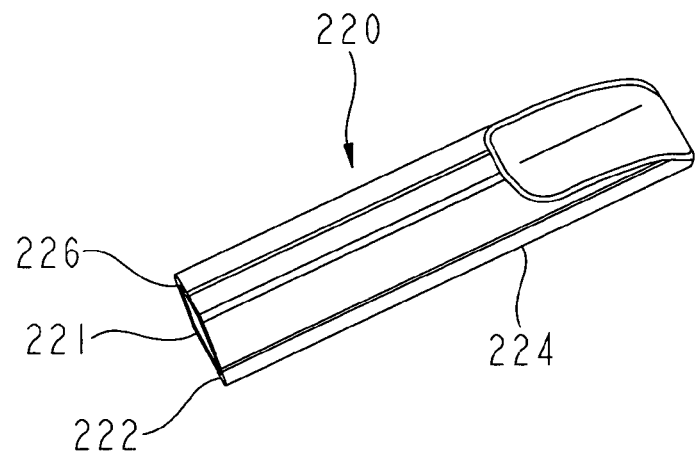
Figure 4A:
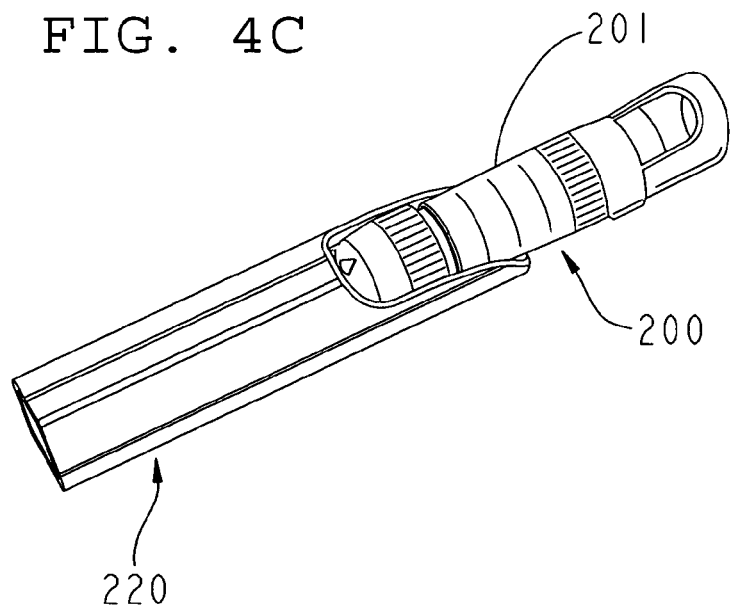

The case bottom 17, best shown in FIG. 3C, includes an automated consolidated test-wand opening 170 for automated meter evaluation of a blood sample, and the visual back-up test wand opening 176. The automated consolidated test-wand opening 170 includes a first side wall 172 and a second side wall 174 that cooperate with the consolidated test wand 200 for sample analysis, as will be described below. The test wand insertion slots 170, 176 for meter and visual measurement are sized and shaped for insertion of a test strip end 202 of the consolidated test wand 200.

The consolidated test wand 200 includes a body portion 201, the test strip end 202 containing a test strip 204, and a cartridge 220. The consolidated test wand 200 is preferably the type described in greater detail in Kloepfer et al., U.S. Patent Publication 2003/0109777 ("the '777 Publication"), and the test strip 204 and the thin film, capillary-augmented sample acquisition process are based on the methods disclosed in Kloepfer et al., U.S. Pat. No. 6,696,240 ("the '240 patent"), which was filed on Oct. 25, 2000 and issued on Feb. 24, 2004, and which has been improved upon by auxiliary mechanical means as disclosed herein. Both the '777 Publication and the '240 patent are incorporated herein by reference.

The right and left side members 20, 21 join the case front 12 to the case back 13, and also have mounting ridges 35 for mounting one or more consolidated test wand cartridges 220 to the case 10, each of the cartridges 220 containing a consolidated test wand 200.

The consolidated test wand cartridge 220 includes a generally cylindrically shaped cavity 224 having a bottom 226, and a pair of longitudinally extending ridges 221, 222 on the exterior of the cavity 224. The cavity 224 of the test wand cartridge 220 is sized and shaped for receiving the test strip end 202 of the consolidated test wand 200. A drying agent can be deposited on the bottom 226 of the interior of the cavity 224 to prevent moisture from affecting the test strip 204 mounted in the consolidated test wand 200.

A consolidated test wand 200 comes with the test strip end 202 sealed in the test wand cartridge 220 so that the test strip 204 is protected from the environment until the consolidated test wand 200 is removed from the test wand cartridge 220. In contrast to the commonly used method of delivering multiple test strips in a single vial, each test strip 204 is protected from the effects of the outside environment, such as dirt, dust and moisture, until the test strip 204 is to be used. For example, in a vial having twenty test strips, every time the vial is opened to retrieve one test strip for testing, all of the test strips are exposed to the environment. As a consequence, by the time the last test strip is being used, it has been exposed to the environment on at least twenty different occasions due to the twenty times the vial was previously opened to retrieve the nineteen previous test strips and the current test strip. In the present invention, since each consolidated test wand 200 comes sealed in its own test wand cartridge 220, the test strip 204 is only exposed to the environment once when it is being used for testing, greatly diminishing the chance of test results being adversely effected by environmental factors.

In the preferred embodiments, the right side member 20 and the left side member 21 are identical or mirror images of each other. Thus, the following description is given for the right side member 20 but applies equally to the left side member 21. The mounting ridges 35 on the right side member 20 include a first longitudinally extending ridge 141, a second longitudinally extending ridge 142, a third longitudinally extending ridge 143 and a fourth longitudinally extending ridge 144 that are each sized and configured for cooperatively receiving multiple test wand cartridges 220, each of the test wand cartridges 220 holding one consolidated test wand 200. Each test wand cartridge 220 includes the first longitudinally extending ridge 221 and the second longitudinally extending ridge 222. The four side member longitudinally extending ridges 141, 142, 143, 144 are equally spaced so the two cartridge ridges 221, 222 can be fit over either the first and second side member ridges 141, 142, or alternatively over the second and third side member ridges 142, 143, or alternatively over the third and fourth side member ridges 143, 144. FIG. 1 shows a test wand cartridge 220 holding a test wand 200 attached to the case 10 with the first longitudinally extending ridge 221 of the cartridge 220 attached to the second ridge 142 of the right side member 20 and the second longitudinally extending ridge 222 of the cartridge 220 attached to the third ridge 143 of the right side member 20. Multiple test wands 220 can be attached longitudinally along each of the right side member 20 and the left side member 21. When using the first and second ridges 141, 142 to attach one set of test wand cartridges 220, and the third and fourth ridges 143, 144 for attaching another set of test wand cartridges 220, two test wand cartridges 220 can be attached side-by-side latitudinally on the side member 20 allowing twice the number of test wand cartridges 220 to be attached to the case 10.

Figure 5:
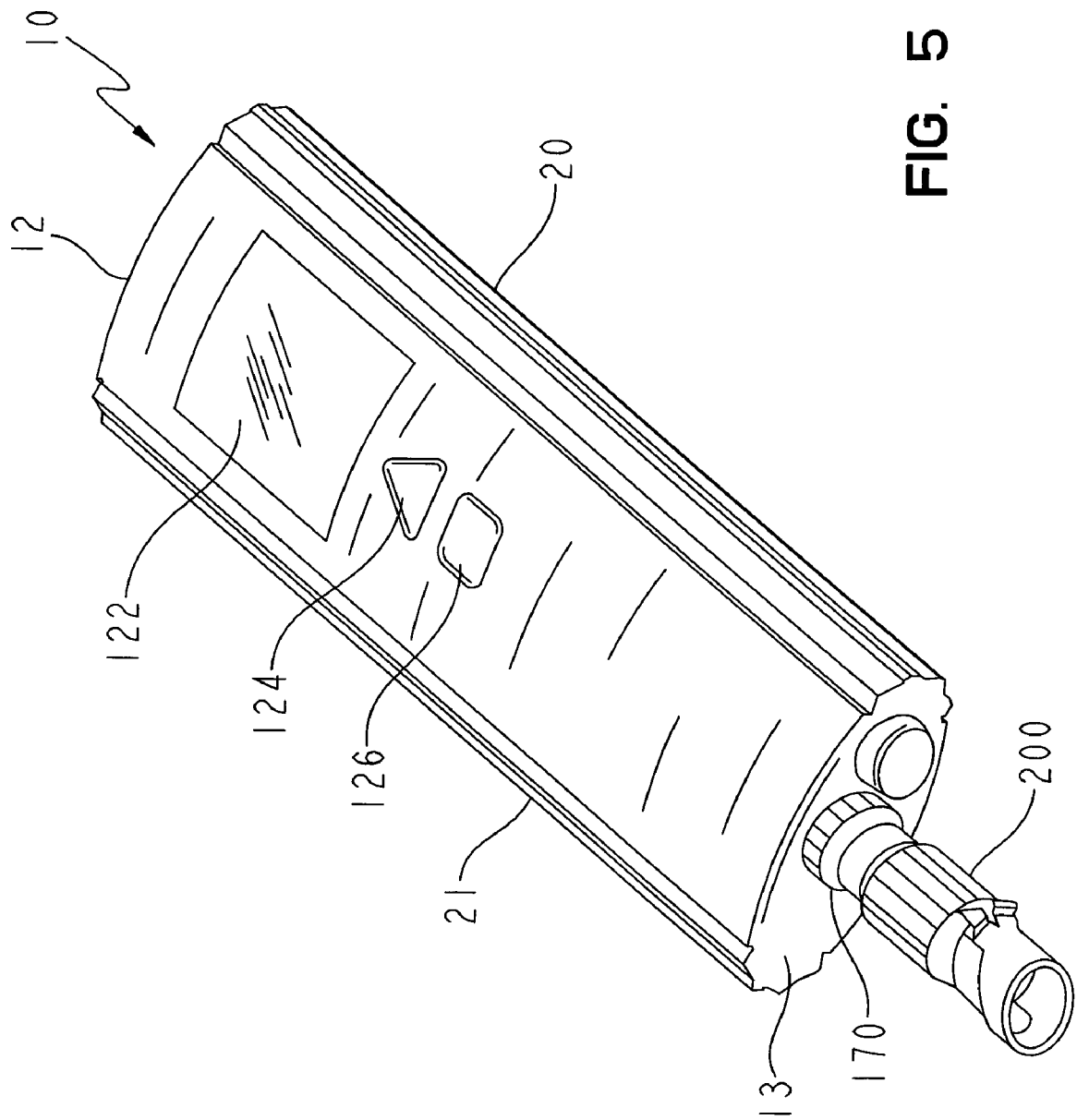
FIG. 5 is a perspective view of the consolidated test wand inserted in the automated test wand opening of the meter.

The meter 10 and consolidated test wand 200 work cooperatively to provide a reading of an analysis fluid, for example, a blood sample obtained by the user. FIG. 5 shows the consolidated test wand 200 inserted in the automated test wand insertion slot 170 of the meter 10. As the meter 10 receives the test strip end 202 of the consolidated test wand 200, the meter 10 and test wand 200 cooperatively manipulate the test strip 204 to perform fluid separation and to facilitate the reading of the reagent on the test strip that has been exposed to the analysis fluid.

Figure 6:
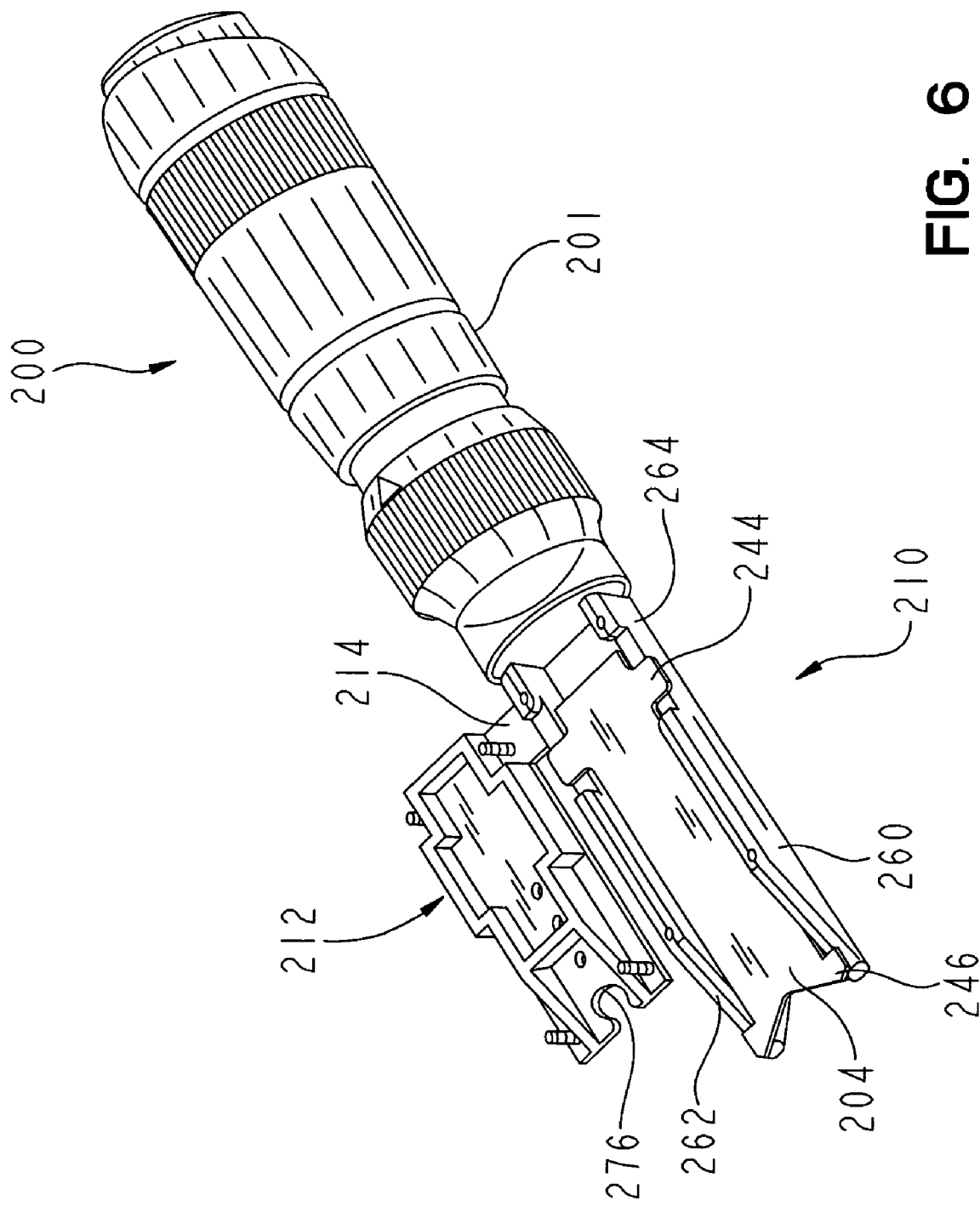
FIG. 6 is a perspective view of the consolidated test wand with the test strip inserted and the test strip holder in the open position.
Figure 7:
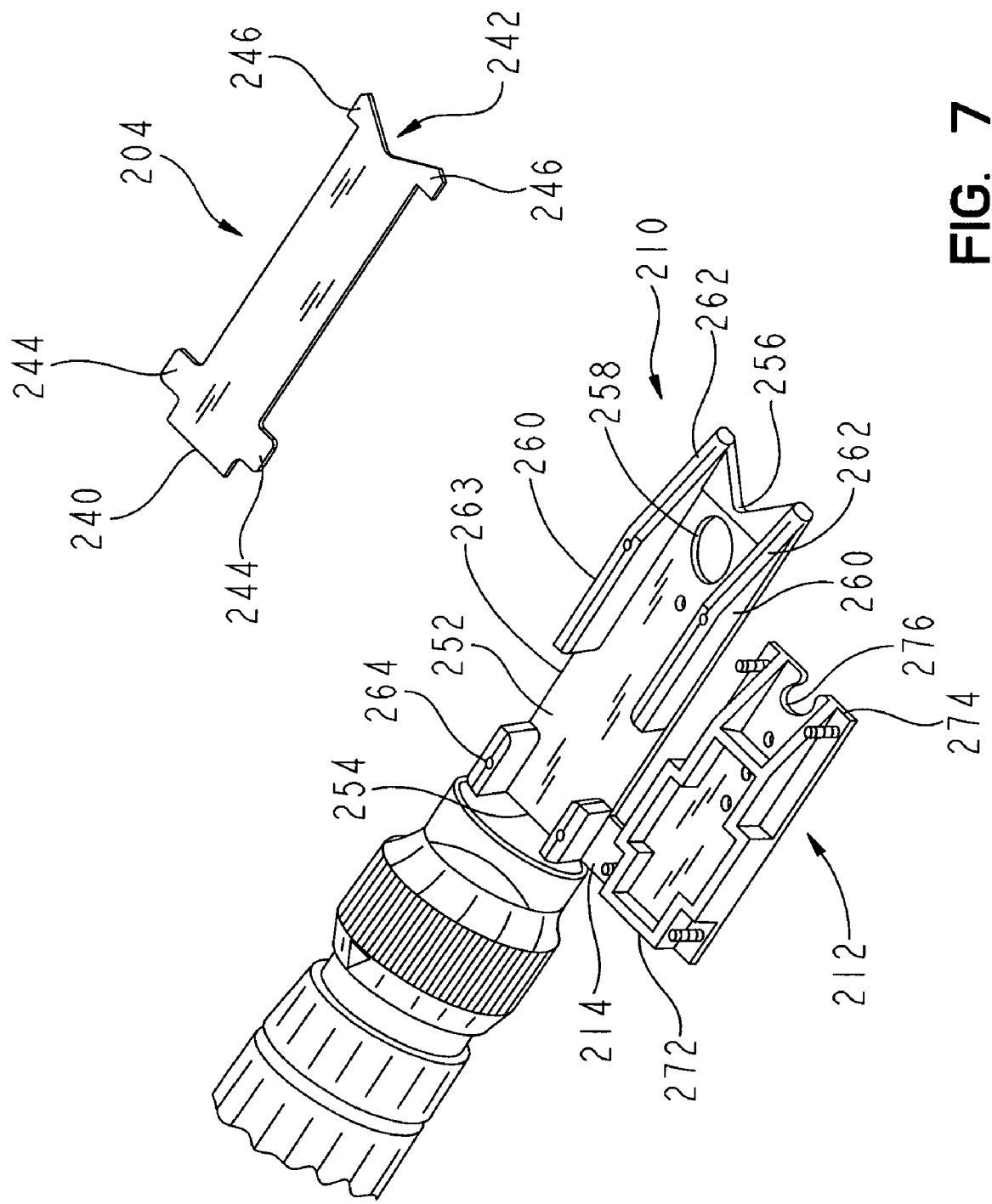
FIG. 7 is a perspective view of the consolidated test wand with the test strip holder in the open position and the test strip removed.

The test strip end 202 of the consolidated test wand 200 includes four primary components: the test strip 204, a test strip holder 210 and a test strip retainer 212. In the preferred embodiments, the test strip end 202 also includes a hinge mechanism 214 for hingedly coupling the test strip holder 210 and the test strip retainer 212. The test strip retainer 212 is movable between an open position (see e.g. FIGS. 5-6) and a closed position (see e.g. FIGS. 8 and 12). When the test strip retainer 212 is in its closed position, the test strip 204 is sandwiched between the test strip retainer 212 and the test strip holder 210 to maintain the test strip 204 in the desired position on the consolidated test wand 200.

The test strip 204 includes a proximal end 240 and a generally concave shaped distal end 242. Generally, blood is placed on the test strip 204 at the distal end 242 and through capillary or mechanical forces is caused to flow toward the proximal end 240. The test strip 204 is designed to separate the colored (primarily erythrocyte) component of the blood from the clear, primarily plasma components of the blood, to provide a generally clear analyte fluid, that can then be reacted with reagents contained on the test strip 204 to form a colored reaction product that can then be analyzed either visually, or through the use of the meter 10.

The embodiments for cooperation between the meter 10 and the consolidated test wand 200 for processing a blood sample, described below, each include steps where the reagent in the chemistry of the test strip 204 is exposed to the sample to react with the analyte of the sample, the exposed reagent is then moved into the optical path of the meter for a reading and/or the unwanted parts of the sample are cleared from the exposed reagent, enabling an optical measurement by the meter 10 of the exposed reagent.

The test strip 204 and the test strip end 202 of the consolidated test wand 200 include a collection component that comprises an inlet, a film containing the reagents, and a wicking structure. When a fluid of interest is applied at the inlet, the wicking structure draws the fluid from the inlet and over the film by exerting capillary or mechanical forces upon the fluid. The reagents on the film react with the desired analyte from the fluid as the fluid is drawn over the film. The wicking mechanism can be structured to exert sufficient force on the fluid to effectively sweep the film free of particulate matter (e.g. erythrocytes) of the fluid, thereby clearing the optical path for an optical measurement of the exposed reagent on the film. The test strip end 202 of the consolidated test wand 200, the test strip 204, and the test strip receiving aperture 170 of the meter 10 are sized and shaped to cooperatively perform the above described functional steps.

In the case where the fluid of interest is blood, the test strip 204 is designed to separate the colored (primarily hemoglobin) components of the blood from the clear, primarily plain components of the blood, to provide a generally clear analyte fluid, that can then be reacted with reagents contained on the test strip 204 to form either a colorimetric or non-colorimetric reaction product that can then be analyzed either visually, or through the use of a meter 10.

The first embodiment to be described for cooperative processing of a blood sample by the meter 10 and the consolidated test wand 200 is the panel separation method shown in FIGS. 5-10 and 19.

Figure 9A:
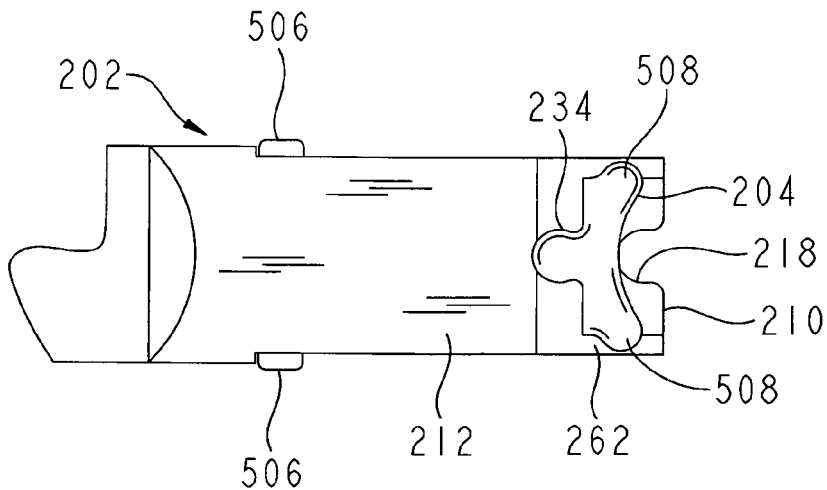
FIGS. 9 A-B are top and side views, respectively, of the test strip end of the consolidated test wand and the test strip for use in the separation method after being inserted in the meter.
Figure 9B:
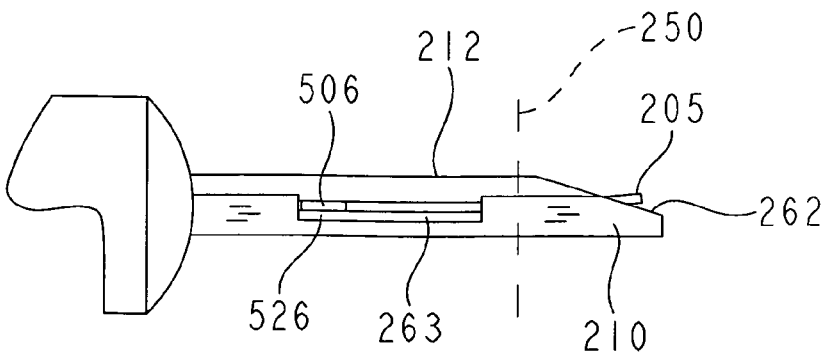
Figure 10:
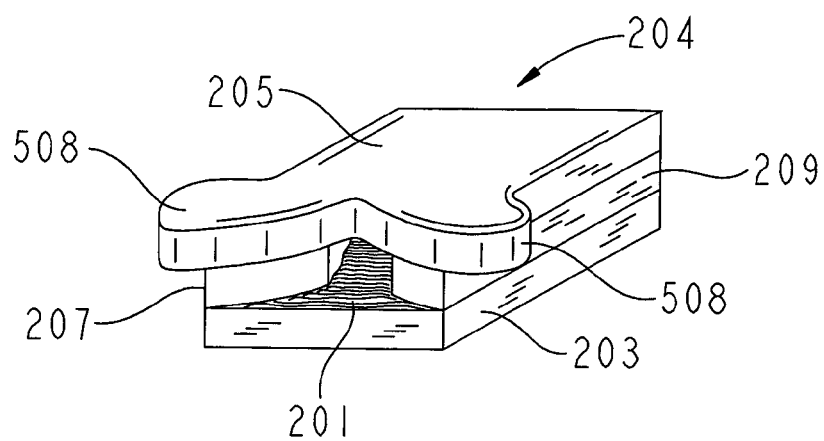
FIG. 10 is a blown up view of the test strip used in the separation method.

The test strip 204 used in the panel separation method includes an upper panel 205; a lower panel 203; a left side spacer 207 and a right side spacer 209. The upper and lower panels 205, 203 are hingedly attached at the proximal end 240 of the test strip 204 and are preferably made of transparent plastic. The upper and lower panels 203, 205 can be attached by various methods known in the art, including, for example, double stick tape or ultrasonic welding. The left and right side spacers 207, 209 separate the upper and lower panels 205, 203 creating a channel 201. FIG. 9 shows an exemplary, but out of proportion cross-section of the distal end 242 of the test strip 204 showing the channel 201. The channel 201 is surrounded on the left and right by the left and right side spacers 207, 209, respectively, and surrounded on the top and bottom by the upper and lower panels 205, 203, respectively. A reagent 312 is deposited in the channel 201. During use, the user introduces an analysis fluid 314, such as blood, into the channel 201 which reacts with the reagent 312.

The test strip holder 210 includes a generally planar base 252 having a proximal end 254, and a generally concave shaped distal end 256 to facilitate the introduction of blood to the test strip 204. The base 252 includes an optical path aperture 258 through which an optical measurement may be taken by the meter 10 when the test strip portion 202 of the consolidated test wand 200 is fully inserted in the meter 10. Several different types of optical measurements can be taken, including but not limited to transmittance, reflectance, luminescence or fluorescence measurements. The test strip holder 210 also includes a pair of upstanding side walls 260 that extend along the sides of the base 252 from the proximal end 254 to the distal end 256. Each of the side walls 260 includes an arm slot 264 and a ramp shaped distal end 262. The base 252 and side walls 260 are sized and shaped so that, prior to use, the test strip 204 rests on the base 252 between the side walls 260 with the arms 506, 526 of the test strip 204 extending outward in the arm slots 264, and the feet 508 of the test strip 204 extending outward on the distal side of the ramped shaped distal end 262 of the side walls 260.

The test strip retainer 212 is designed to matingly engage with the test strip holder 210, for retaining the test strip 204 in the desired position. The test strip retainer 212 has a proximal end 272, and a distal end 274. The distal end 274 of the test strip retainer 212 includes a concave cut-out portion 276 for both facilitating the introduction of blood onto the test strip 204, and for providing a clear optical path for an optical measurement by the meter 10 when the test strip portion 202 of the consolidated test wand 200 is fully inserted in the meter 10.

Figure 8A:
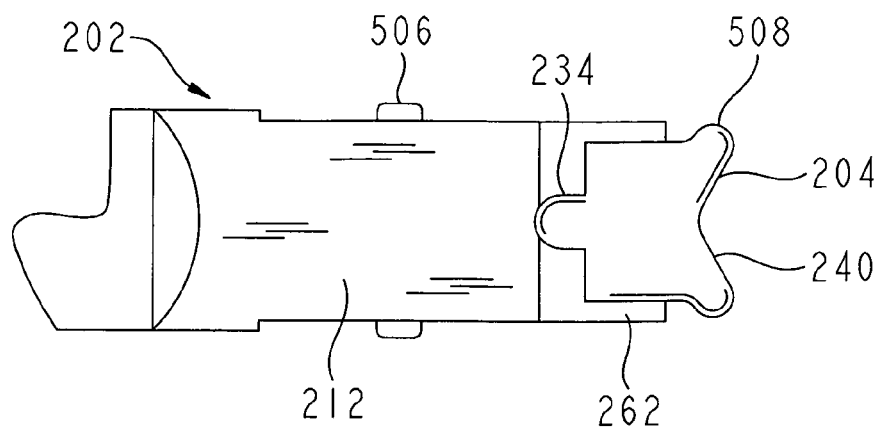
FIGS. 8 A-B are top and side views, respectively, of the test strip end of the consolidated test wand and the test strip for use in the separation method prior to being inserted in the meter.

The upper and lower panels 205, 203 of the test strip 204 are shown separately in FIG. 19. The upper panel 205 includes a proximal end 502 and a distal end 504. The lower panel 203 includes a proximal end 522 and a distal end 524. The upper panel 205 further includes a pair of latitudinally extending arms 506 and a pair of latitudinally extending feet 508. The lower panel 203 also includes a pair of latitudinally extending arms 506. The arms 506, 526 extend outward from the main body of the upper and lower panels 203, 205 further than the feet 508 as shown in FIGS. 8A, 9A and 19. The feet 508 extend outward far enough to engage the ramped surfaces 262 of the side walls 260, but not so far as to engage the side walls 172, 174 of the automated test wand opening 170 of the meter 10 when the test strip end 202 of the consolidated test wand 200 is inserted in the automated test wand opening 170 of the meter 10. The arms 506, 526 extend outward far enough to engage the side walls 172, 174 of the automated test wand opening 170 of the meter 10 when the test strip end 202 of the consolidated test wand 200 is inserted in the automated test wand opening 170 of the meter 10.

Figure 8B:
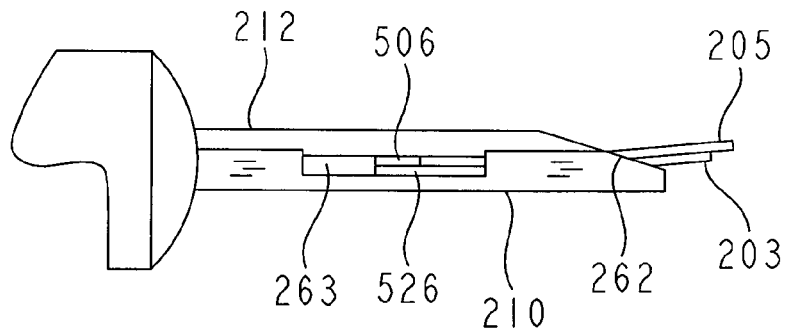

FIGS. 8A, 8B, and 10A show the test strip end 202 of the consolidated test wand 200 and the test strip 204 before the consolidated test wand 200 is inserted in the automated test wand opening 170 of the meter 10. The feet 508 of the upper panel 205 of the test strip 204 extend distally beyond the ramped distal ends 262 of the side walls 260 of the test strip holder 210, and the arms 506, 526 are located near the distal end of the arm slots 264. At this point, the upper and lower panels 205, 203 of the test strip 204 are generally parallel to each other, separated by the spacers 207, 209.

As the test strip end 202 of the consolidated test wand 200 is inserted into the meter 10, the arms 506, 526 of the test strip 204 engage the side walls 172, 174 of the automated test wand opening 170 of the meter 10. As the test strip end 202 is inserted further into the meter 10, the arms 506, 526 are pushed in the proximal direction in the arm slots 264 by the side walls 172, 174 of the automated test wand opening 170. This movement of the arms 506, 526 pulls the upper panel 205 and lower panel 203 in the proximal direction relative to the test strip holder 210 and retainer 212. This movement causes the entire test strip 204 to move in the proximal direction relative to the test strip holder 210 and retainer 212. As the test strip 204 moves in the proximal direction relative to the test strip holder 210, the feet 508 of the upper panel 205 engage the ramped sides 262 of the side walls 260 of the test strip holder 210 causing the upper panel 205 to be pulled up and away from the lower panel 203 of the test strip 204. The separation of the upper and lower panels 203, 205 of the test strip 204 causes the surface to volume ratio in the distal end of the channel 201 to decrease relative to the proximal end of the channel 201 which creates a capillary gradient pulling the analysis fluid 314 in the proximal direction in the channel 201. This pulls the analysis fluid 314 off the reagent 312 in the distal portion of the channel 201 of the test strip 204 which creates an optical path 250 that is unobstructed by the analysis fluid 314.

FIGS. 8A, 8B and 10B show the test strip end 202 of the consolidated test wand 200 and the test strip 204 after the consolidated test wand 200 has been inserted in the automated test wand opening 170 of the meter 10. The optical path 250 extends through the cutout portion 276 of the test strip retainer 212, the upper panel 205 of the test strip 204, the reagent 312 which has previously reacted with the analysis fluid 314, the lower panel 203 of the test strip 204, and the optical path aperture 258 of the test strip holder 210. The meter 10 can then measure the desired characteristics of the reagent 312 using the optical path 250 which is unobstructed by the analysis fluid 314.

The second method to be described for cooperative processing of a blood sample by the meter 10 and the consolidated test wand 200 is called the panel sheer method shown in FIGS. 11-14 and 20. For the panel sheer method, the test strip holder 210 and the test strip retainer 212 can be the same as used in the panel separation method described above, except that it is not necessary that the side walls 260 include the ramp shaped distal ends 262.

Figure 14:
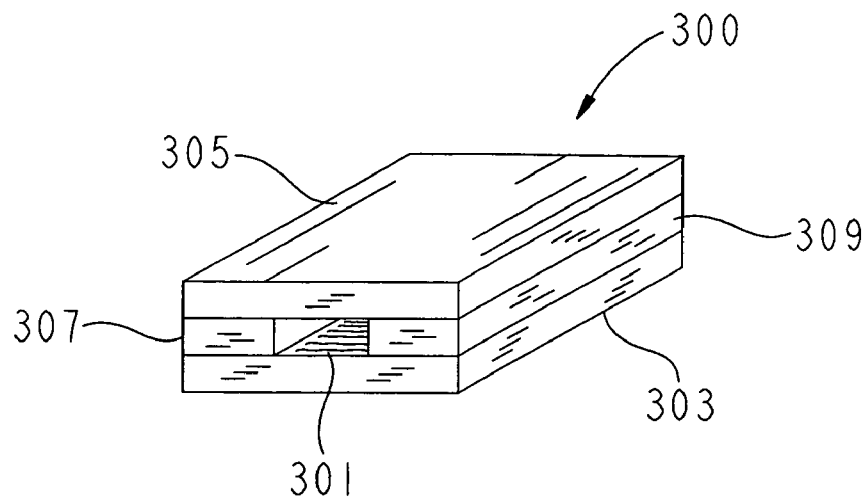
FIG. 14 is a blown up view of the test strip used in the slide method.

The panel sheer method uses a sheer test strip 300 shown in one or more of FIGS. 11-14 and 20 which is similar to the test strip 204 discussed previously. The sheer test strip 300 (FIG. 14) has a proximal end 340 and a distal end 342, and includes an upper panel 305 (FIG. 14); a lower transparent panel 303 FIG. 13B); a left side spacer 307 (FIG. 14) and a right side spacer 309. The left and right side spacers 307, 309 separate the upper and lower panels 305, 303 creating a channel 301. FIG. 14 shows an exemplary, but out of proportion cross-section of the distal end 342 of the sheer test strip 300 showing the channel 301 (FIG. 14). The channel 301 is surrounded on the left and right by the left and right side spacers 307, 309, respectively, and surrounded on the top and bottom by the upper and lower panels 305, 303, respectively. A reagent 312 (FIGS. 11A and 11B) is deposited in the channel 301. During use, the user introduces an analysis fluid 314 (FIGS. 11A and 11B), such as blood, into the channel 301 which reacts with the reagent 312.

Figure 20A:
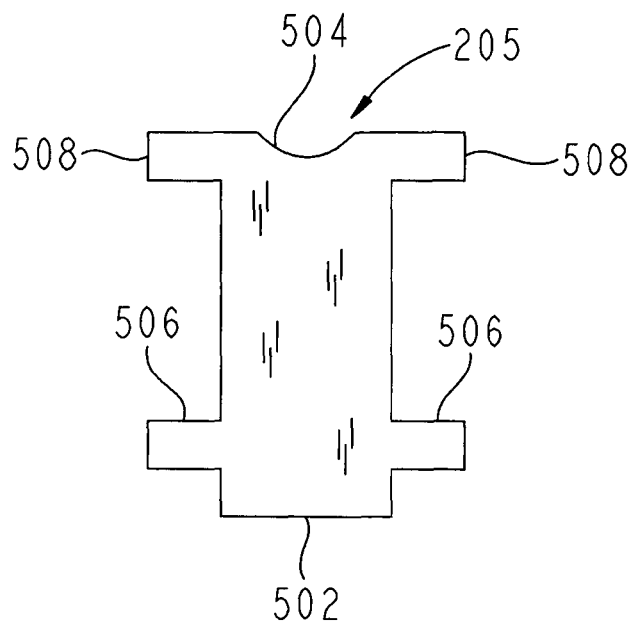
FIGS. 20 A-B are blown up perspective views of the top and bottom layers, respectively, of the test strip used in the panel separation method.
Figure 20B:
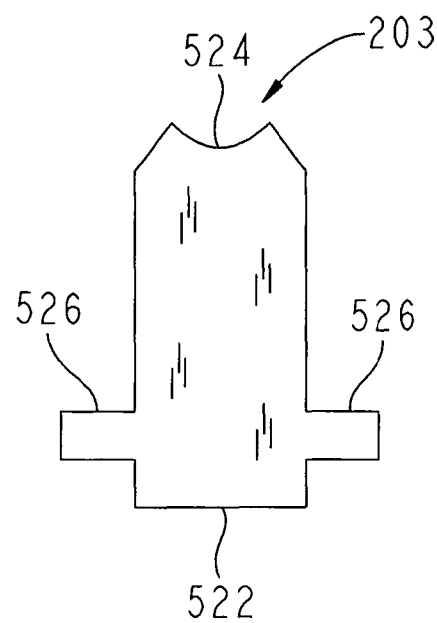

The upper and lower panels 305, 303 of the sheer test strip 300 are shown separately in FIG. 20. The upper panel 305 includes a proximal end 302 and a distal end 304. The lower panel 303 includes a proximal end 322 and a distal end 324. The upper panel 305 further includes a pair of longitudinally extending arms 306, enabling the upper panel 305 to be slid independently of the lower panel 303. The arms 306 extend outward from the main body of the upper panel 305 far enough to engage the side walls 172, 174 of the automated test wand opening 170 of the meter 10 when the test strip end 202 of the consolidated test wand 200 is inserted in the automated test wand opening 170 of the meter 10.

Figure 11A:
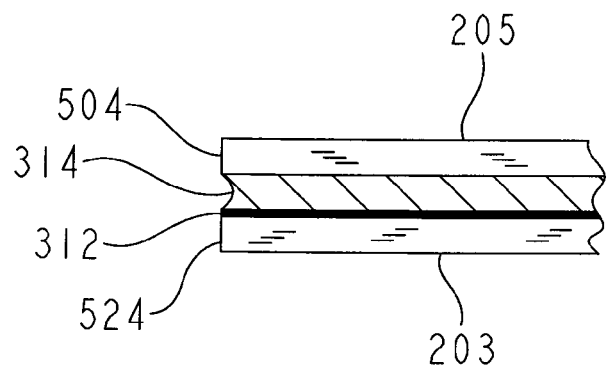
FIGS. 11 A-B are blown up side views of the test strip used in the separation method prior to being inserted and after being inserted in the meter, respectively.
Figure 11B:
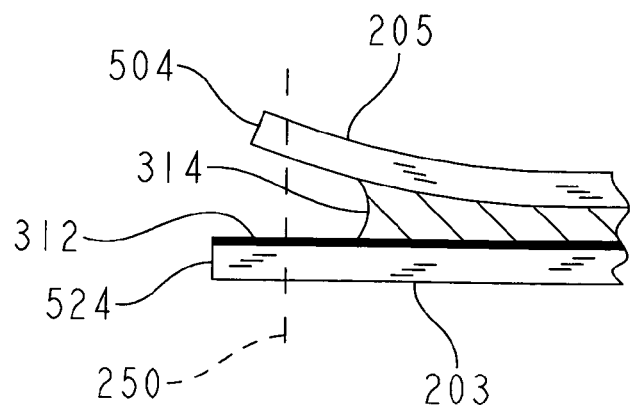

FIGS. 11A, 11B and 14A show the test strip end 202 of the consolidated test wand 200 and the sheer test strip 300 before the consolidated test wand 202 is inserted in the first consolidated test wand opening 170 of the meter 10 for the panel sheer method. The distal end 304 of the upper panel 305 and the distal end 324 of the lower panel 303 extend generally the same distance to the distal end 256 of the test strip holder 210, and the latitudinally extending arms 306 of the upper panel 305 are located near the distal end of the arm slots 264 of the side walls 260. The upper and lower panels 305, 303 of the sheer test strip 300 are generally parallel to one another and the analysis fluid 314 extends to the distal ends 304, 324 of the upper and lower test strip panels 305, 303.

As the test strip end 202 of the consolidated test wand 200 is inserted into the meter 10, the latitudinally extending arms 306 of the upper panel 305 of the sheer test strip 300 engage the side walls 172, 174 of the automated test wand opening 170 of the meter 10. As the test strip end 202 is inserted further into the meter 10, the arms 306 are pushed in the arm slots 264 toward the proximal end 254 of the test strip holder 210 by the side walls 172, 174 of the automated test wand opening 170. The movement of the arms 306 pulls the upper panel 305 in the proximal direction relative to the lower panel 303, the test strip holder 210 and the test strip retainer 212. The sliding of the upper panel 305 in the proximal direction creates a capillary force which pulls the analysis fluid 314 in the channel 301 along with the upper panel 305 in the proximal direction, removing the analysis fluid 314 from a portion of the reagent 312 in the channel 301 on the distal end 324 of the lower transparent panel 303 which creates an optical path 350 that is unobstructed by the analysis fluid 314.

Figure 12A:
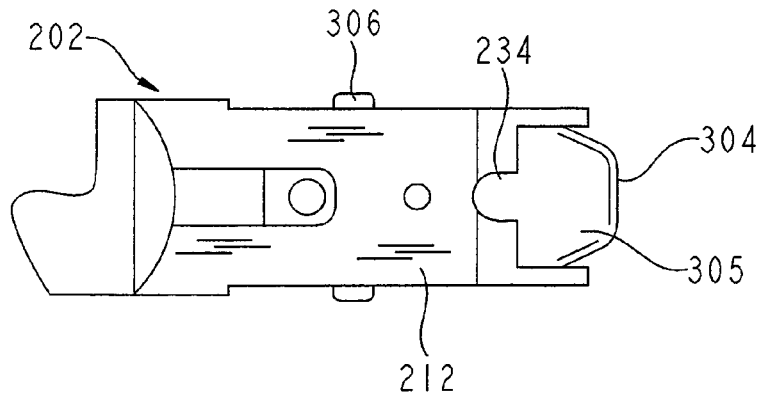
FIGS. 12 A-B are top and side views, respectively, of the test strip end of the consolidated test wand and the test strip for use in the slide method prior to being inserted in the meter.
Figure 12B:
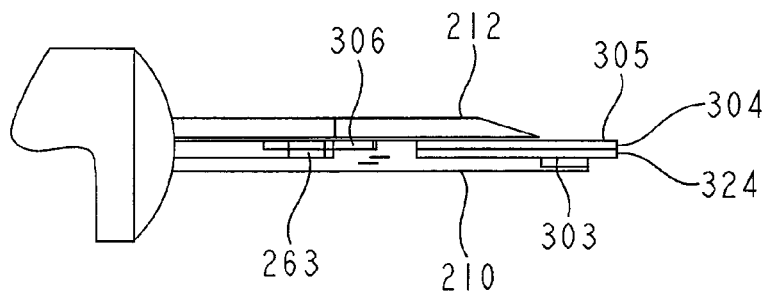
Figure 13A:
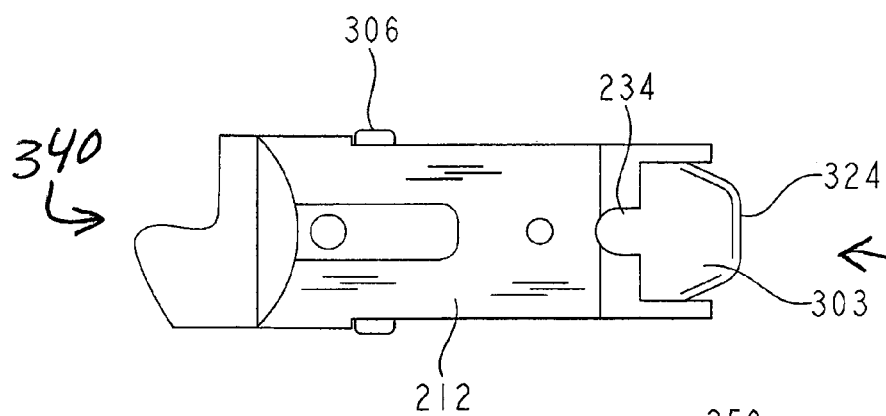
FIGS. 13 A-B are top and side views, respectively, of the test strip end of the consolidated test wand and the test strip for use in the slide method after being inserted in the meter.
Figure 13B:
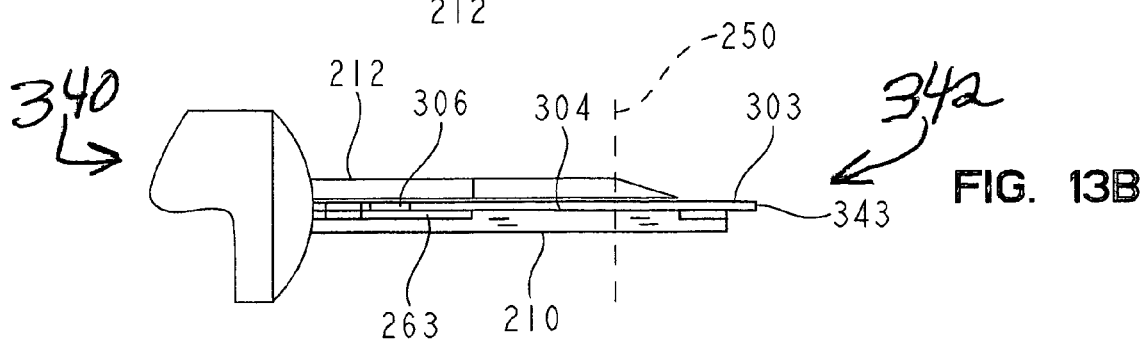

FIGS. 12A, 12B and 14B show the test strip end 202 of the consolidated test wand 200 and the test strip 300 after the consolidated test wand 200 has been inserted in the automated test wand opening 170 of the meter 10. The optical path 350 extends through the cutout portion 276 of the test strip retainer 212, the reagent 312 which has previously reacted with the analysis fluid 314 and has now been cleared of the analysis fluid 314, the lower panel 303, and the optical path aperture 258 of the test strip holder 210. Note, in the panel sheer method, the upper panel 305 of the sheer test strip 300 is not in the optical path 350. The meter 10 can then measure the desired characteristics of the reagent 312 using the optical path 250 which is unobstructed by the analysis fluid 314.

Figure 15A:
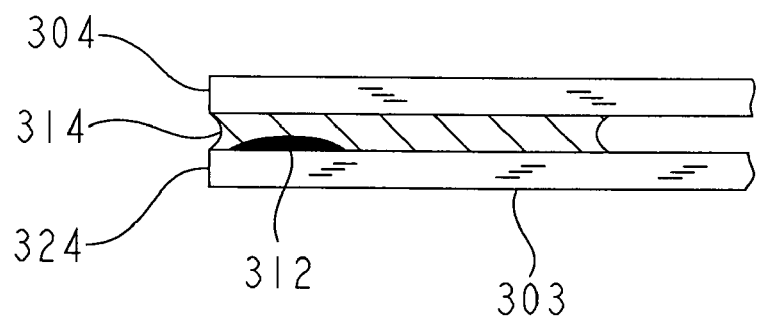
FIGS. 15 A-B are blown up side views of the test strip used in the slide method prior to being inserted and after being inserted in the meter, respectively.
Figure 15B:
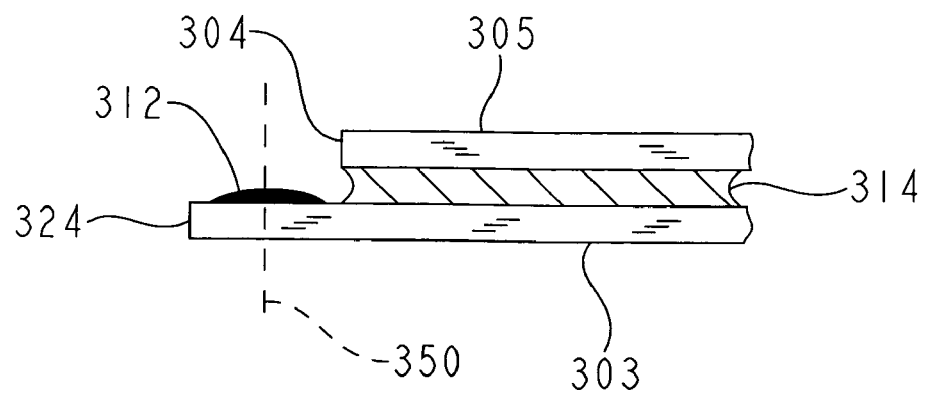
Figure 16:
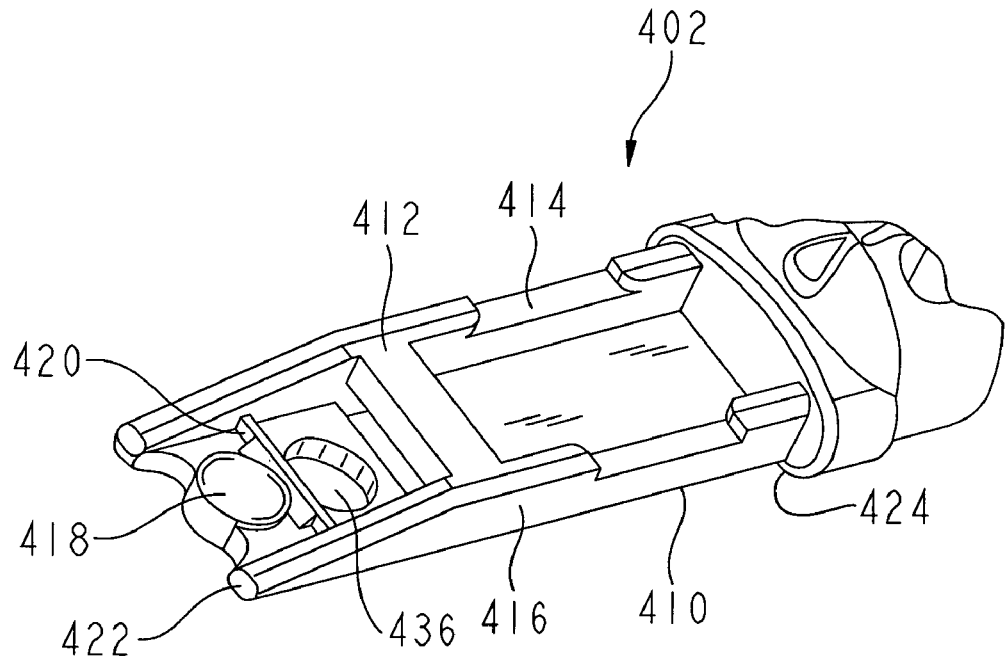
FIG. 16 is a blown up perspective view of the test strip end of the consolidated test wand used in the wiper method.
Figure 17:
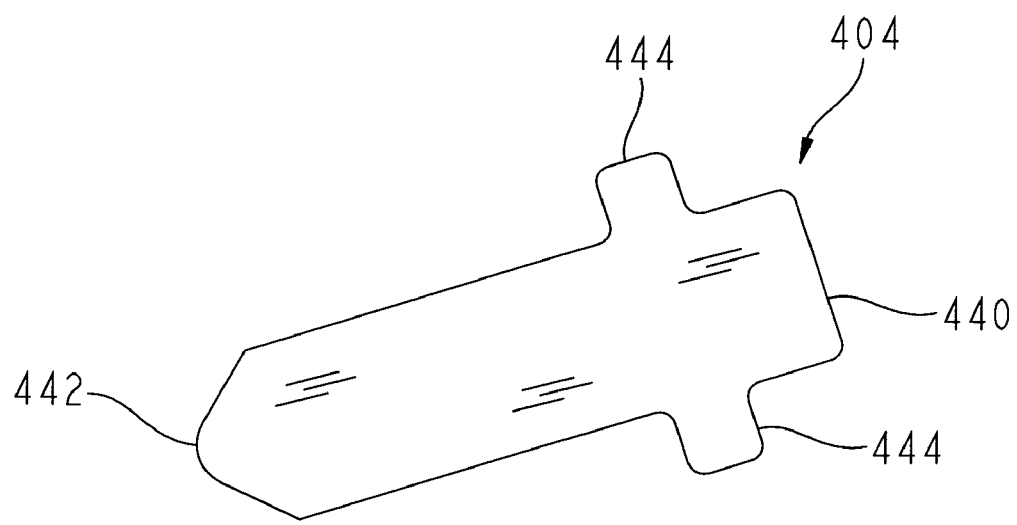
FIG. 17 is a blown up perspective view of the test strip used in the wiper method.

The third method to be described for cooperative processing of a blood sample by the meter 10 and the consolidated test wand 200 is called the wiper method shown in FIGS. 15-18. FIG. 15 shows a wiper test strip end 402 of the consolidated test wand used in the wiper method, and FIG. 16 shows a wiper test strip 404 used in the wiper method.

The wiper test strip end 402 of the consolidated test wand 200 used in the wiper method is similar to the test strip end 202 described above for the panel separation and panel sheer methods. The wiper test strip end 402 includes a test strip holder 410 and a test strip retainer 412, the test strip holder 410 having a distal end 422 and a proximal end 424. The wiper test strip holder 410 includes an upward forcing proximal protrusion 430, and a pair of upstanding side walls 416 for positioning the wiper test strip 404, and maintaining it on the holder 410. The upstanding walls 416 include arm slots 414. The distal end 422 of the test strip holder 410 includes a generally circular sample application pad 418 that facilitates the introduction of blood to the wiper test strip 404. On the proximal side of the application pad 418, the wiper test strip holder 410 includes a wiper 420. On the proximal side of the wiper 420, the wiper test strip holder 410 includes an optical path aperture 436 for measurement by the meter 10 when the wiper test strip end 402 of the consolidated test wand 200 is fully inserted in the meter 10.

The wiper test strip retainer 412 is designed to matingly engage with the wiper test strip holder 410, for retaining the wiper test strip 404. The wiper test strip retainer 412 is movable between an open position that permits the test strip 404 to be inserted onto and/or removed from its engagement with the test strip holder 410; and a closed position wherein the test strip retainer 412 matingly engages the test strip holder 410 to positionally secure and retain the wiper test strip 404 onto the test strip end 402 of the consolidated test wand 200. The wiper test strip retainer 412 includes a downward forcing distal protrusion 432.

The wiper test strip 404 used in the wiper method includes a single transparent panel with the reagent 312 deposited on the underside 446 of the test strip 404. The test strip 404 has a proximal end 440 and a fluid sample receiving distal end 442. The test strip 404 includes a pair of latitudinally extending arms 444 that are sized and shaped for placement in the arm slots 414 of the test strip holder 410 to position the wiper test strip 404 on the test strip holder 410 and receiver 412, and to allow movement of the wiper test strip 404 during processing to prepare the sample for reading by the meter 10.

Figure 18A:
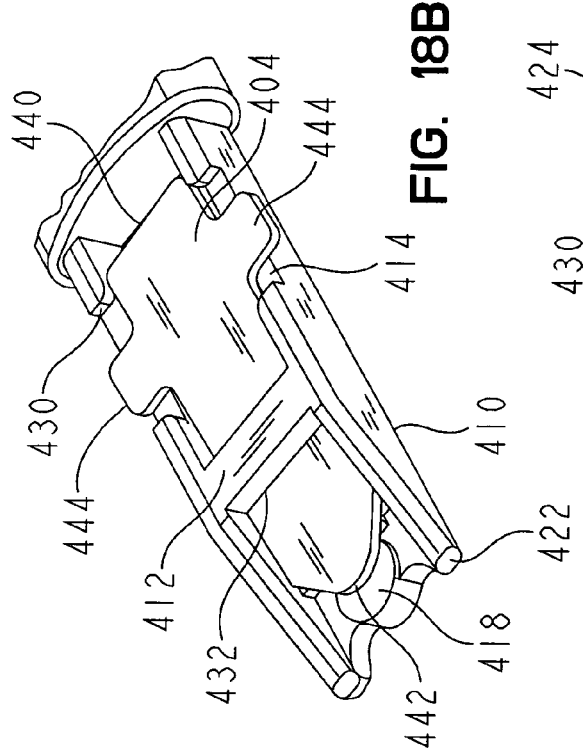
FIGS. 18 A-D are top views of the test strip end of the consolidated test wand and the test strip showing the progression of the wiper method process.
Figure 18B:
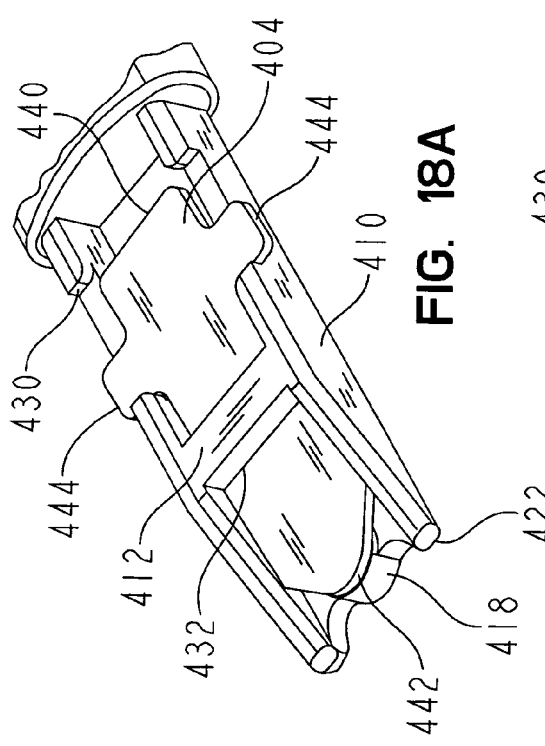
Figure 18C:
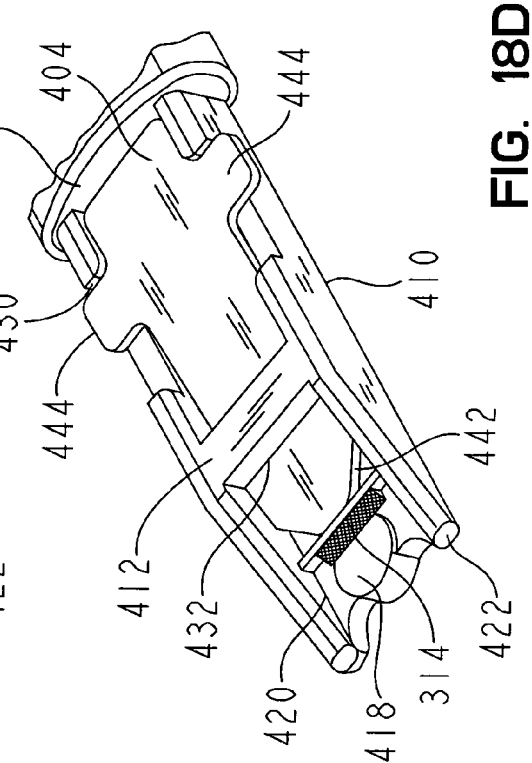

FIGS. 17A and 18A show the test strip end 402 and the test strip 404 before the test strip end 402 is inserted in the first consolidated test wand opening 170 of the meter 10. The distal end 442 of the test strip 404 extends generally to the distal end of the sample application pad 418 at the distal end 422 of the test strip holder 410, and the arms 444 of the test strip 404 are located at the distal end of the arm slots 414 of the test strip holder 410. The downward forcing proximal protrusion 432 of the wiper test strip retainer 412 exerts a downward force on the test strip 404, while the upward forcing proximal protrusion 430 of the wiper test strip holder 410 exerts an upward force on the test strip 404 which together ensure the test strip 404 exerts a downward force on the wiper 420. The sample application pad 418 and the distal end 442 of the test strip 404 form a two panel capillary with open side walls. The user presents the analysis fluid 314 at the distal end of the sample application pad 418 between the top of the sample application pad 418 and the bottom surface 446 of the test strip 404 and through capillary forces the analysis fluid 314 is caused to flow in the proximal direction between the sample application pad 418 and the wiper test strip 404. The reagent 312 on the bottom surface 446 of the wiper test strip 404 reacts with the analysis fluid 314.

Figure 18D:
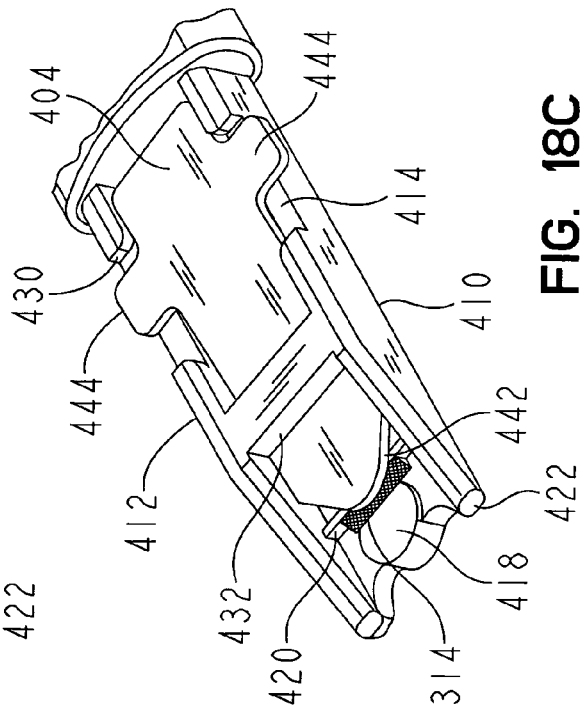
Figure 19A:
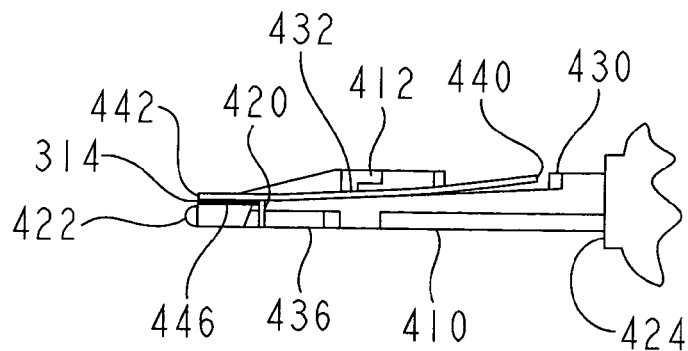
FIGS. 19 A-D are side views of the test strip end of the consolidated test wand and the test strip showing the progression of the wiper method process.
Figure 19B:
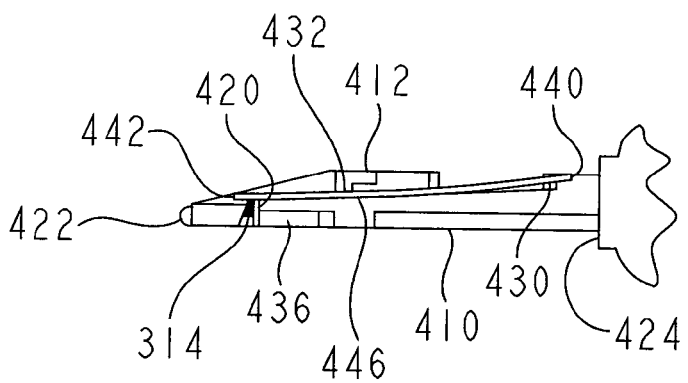
Figure 19C:
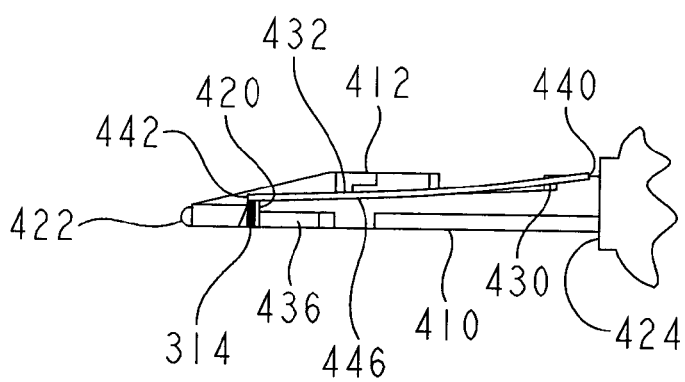
Figure 19D:
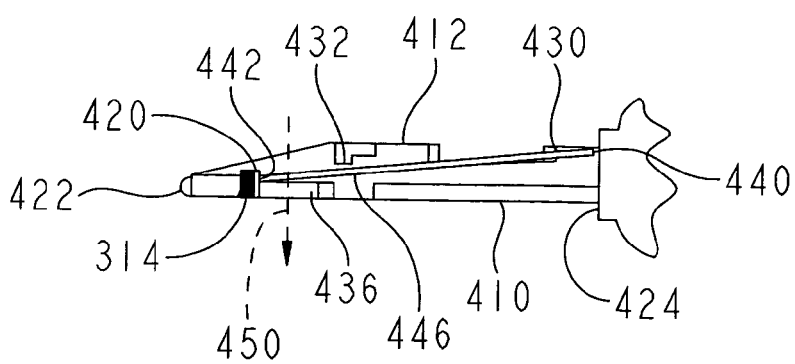

FIGS. 17B-17D and 18B-18D show the progression of the movement of the wiper test strip 404 and the analysis fluid 314 relative to the test strip holder 410 as the test strip end 402 of the consolidated test wand 200 is inserted in the automated test wand opening 170 of the meter 10. As the test strip end 402 of the consolidated test wand 200 is inserted into the meter 10, the arms 444 of the wiper test strip 404 engage the side walls 172, 174 of the automated test wand opening 170 of the meter 10 and are pulled in the proximal direction in the arm slots 414 of the test strip holder 410. This movement causes the wiper test strip 404 to be pulled in the proximal direction relative to the test strip holder 410. The sliding of the wiper test strip 404 in the proximal direction causes the distal end 442 of the wiper test strip 404 to be pulled in the proximal direction off the application pad 418 and across the wiper 420 of the test strip holder 410. The downward force on the wiper test strip 404 due to the distal protrusion 432 of the test strip retainer 412 and the proximal protrusion 430 of the test strip holder 410 causes the wiper test strip 404 to exert a downward force on the wiper 420 which causes the wiper 420 to wipe the analysis fluid 314 off the bottom surface 446 of the wiper test strip 404 leaving only the reagent 312 that has been exposed to the analysis fluid 314 on the bottom surface 446 of the wiper test strip 404 as it is pulled to the proximal side of the wiper 420. As shown in FIGS. 17D and 18D, when the test strip arms 444 are near the proximal end of the arm slots 414 of the test strip holder 410, an optical path 450 that is unobstructed by the analysis fluid 314 is created that extends through the wiper test strip 404, the reagent 312 which has previously reacted with the analysis fluid 314, and the optical path aperture 436 of the test strip holder 410. Note, in the wiper method, the test strip 404 has only one layer.

In the three methods and embodiments described above, the meter 10 and consolidated test wand 200 work cooperatively to process the analysis fluid 314 deposited on the test wand 200 and prepare the reagent 312 that has been exposed to the analysis fluid 314 for a reading by the meter 10. The meter 10 then takes an optical measurement of the reagent 312.

FIG. 22 shows an alternative embodiment of a consolidated test wand 600 that includes a body portion 601, a test strip end 602 containing a test strip 604, and a cap 620. The consolidated test wand 600 is generally similar to the consolidated test wand 200 except it uses the cap 620 to seal the test strip end 602 from the outside environment before use instead of the cartridge 220 used with the consolidated test wand 200. The cap 620 is hingedly connected to the test strip end 602 of the consolidated test wand 600 by a living hinge 622.

FIG. 23 shows an exploded view of the test strip end 602 of the consolidated test wand 600. The test strip end 602 comprises a circular test strip holder 606, and a base 630 to which the cap 620 is attached. The circular test strip holder 606 includes a cylindrical body 608, a cross member 610 and an extension 612 that extends from the cross member 610. The cross member 610 extends across the interior of the cylindrical body 608. The extension 612 extends in the distal direction from the central portion of the cross member 610. The extension 612 includes a distal end 618 and a shallow depression 614 for the application of an analysis fluid.

The base 630 is connected by the living hinge 622 to the cap 620. The base 630 includes a set of posts 634 that define a cavity 632 that is sized and shaped to accept the circular test strip holder 606. The cavity 632 allows the circular test strip holder 606 to be pushed in the proximal direction (towards the body portion 601).

Figure 24A:
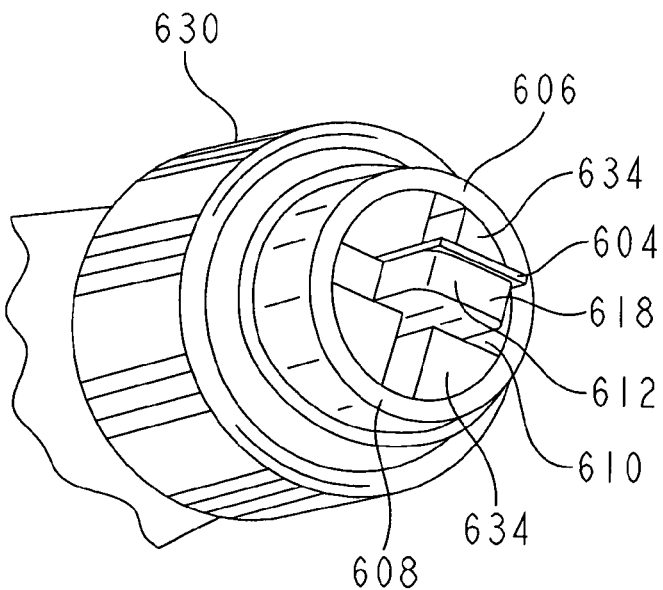
FIGS. 24 A-B show views of the consolidated test wand shown in FIGS. 22 (with the cap not shown) using the slide method before and after insertion in the meter, respectively.

As can be seen in FIG. 24A, before insertion of the test strip end 602 in the first consolidated test wand opening 170 of the meter 10, the circular test strip holder 606 is initially positioned distally on the posts 634 with the distal end 618 of the extension 612 being near the distal end of the test strip 604. The test strip 604 is positioned on the side of the extension 610 having the depression 614 such that the test strip 604 forms the top of the channel 614. The side of the test strip 604 facing the depression 614 contains the reagent 312. In this initial position, a user would apply the analysis fluid 314 between the distal end of the extension 612 and the test strip 604 and capillary forces would pull the analysis fluid 314 in the proximal direction into the channel 614.

As the test strip end 602 of the consolidated test wand 600 is inserted into the meter 10, the cylindrical body 608 of the circular test strip holder 606 engages the side walls 172, 174 of the automated test wand opening 170 of the meter 10. As the test strip end 602 is inserted further into the meter 10, the circular test strip holder 606 is pushed in the proximal direction into the cavity 632 of the base 630 by the side walls 172, 174 of the automated test wand opening 170. The movement of the circular test strip holder 606 pulls the extension 612 in the proximal direction relative to the test strip 604. The sliding of the extension 612 in the proximal direction creates a capillary force which pulls the analysis fluid 314 in the channel 614 along with the extension 612 in the proximal direction, removing the analysis fluid 314 from a portion of the reagent 312 on the test strip 604 which creates an optical path through the reagent 312 that is unobstructed by the analysis fluid 314.

Figure 24B:
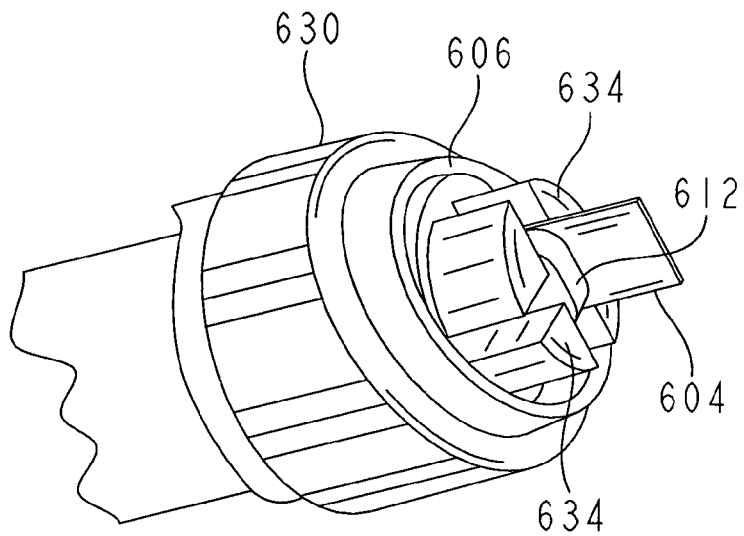
Figure 25:
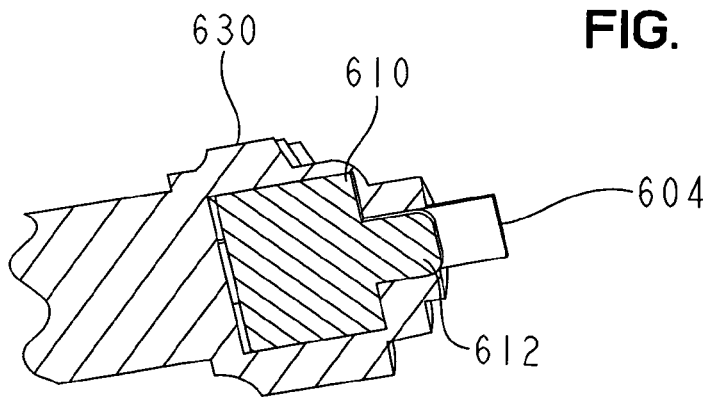
FIG. 25 show a cut away view of the consolidated test wand shown in FIG. 22 after insertion in the meter.
Figure 26:
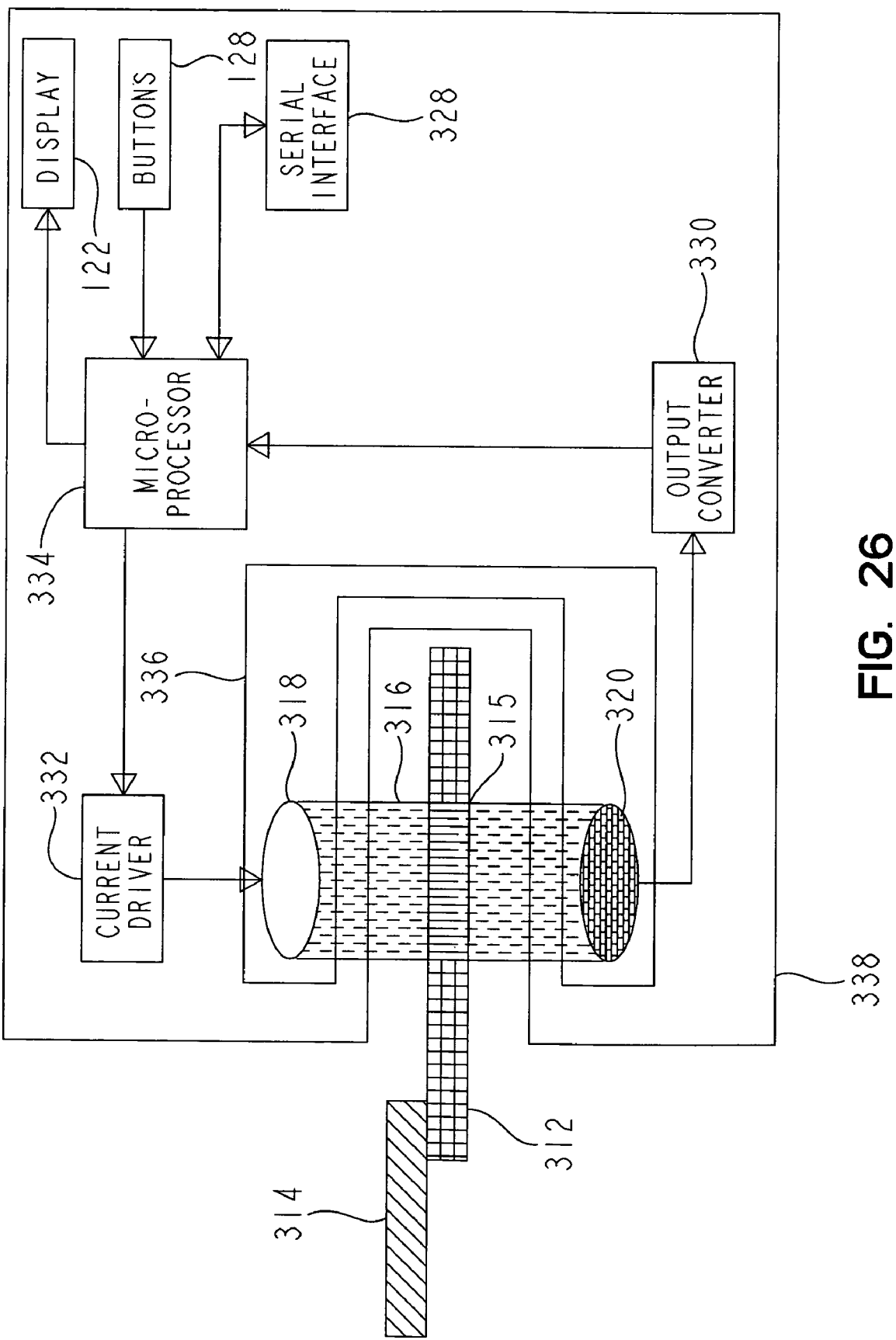
FIG. 26 is a cross-sectional view of the test strip end of the consolidated test wand inserted in a block diagram of the meter.
Figure 27:
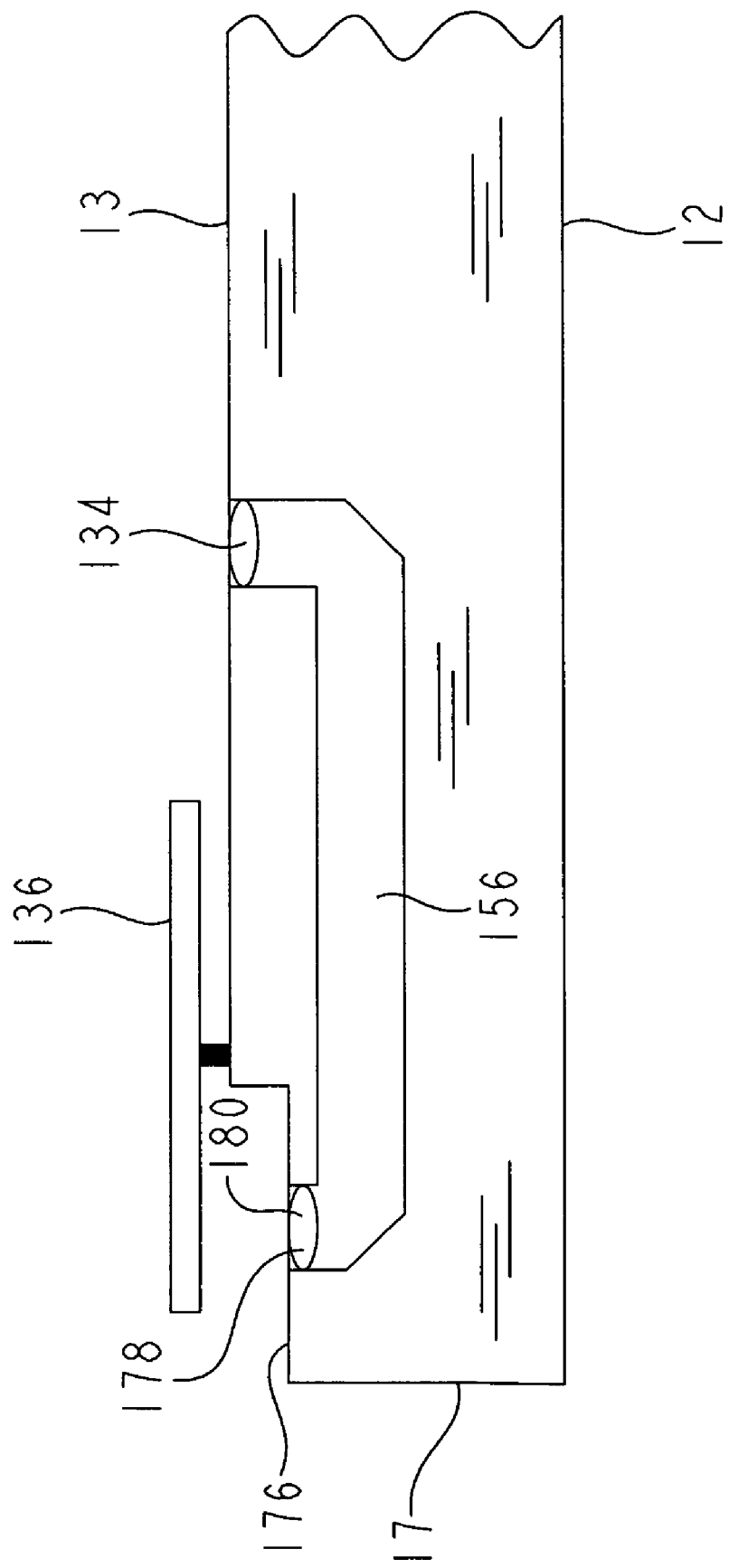
FIG. 27 is a cross-sectional schematic of the light pipe (156) and light pipe openings used in the visual backup system.

FIGS. 24B and 25 show the test strip end 602 of the consolidated test wand 600 and the test strip 604 after the consolidated test wand 600 has been inserted in the automated test wand opening 170 of the meter 10. The optical path extends through the distal end of the test strip 604 and the reagent 312 thereon which has previously reacted with the analysis fluid 314 and has now been cleared of the analysis fluid 314 which was pulled in the proximal direction along with the extension 612. The meter 10 can then measure the desired characteristics of the reagent 312 on the distal end of the test strip 304.

The meter 10 measures characteristics of the analysis fluid 314 using a reagent 312 through optical measurements, and communicates the results to the user. Reflectance measurements measure the amount of light from a light source that is reflected by or through the exposed reagent 314 to a light detector. Fluorescence or luminescence measures the amount of radiation produced or emitted from the exposed reagent 314 to a light detector. In the preferred embodiment, the meter 10 uses a transmission measurement as shown in the schematic diagram of FIG. 21.

Using an optical measurement and the capillary techniques of the present invention enables fluid analysis with an ultra-miniaturized fluid sample. This can be a very important feature in many applications, such as blood analysis for diabetics, which require frequent fluid samples. Reasons for these benefits include that the capillary techniques confine the fluid sample to a very small space thus requiring less fluid to present an adequate sample, and for the case of transmittance measurements, the blooming problem encountered with reflectance measurements is avoided.

Figure 21A:
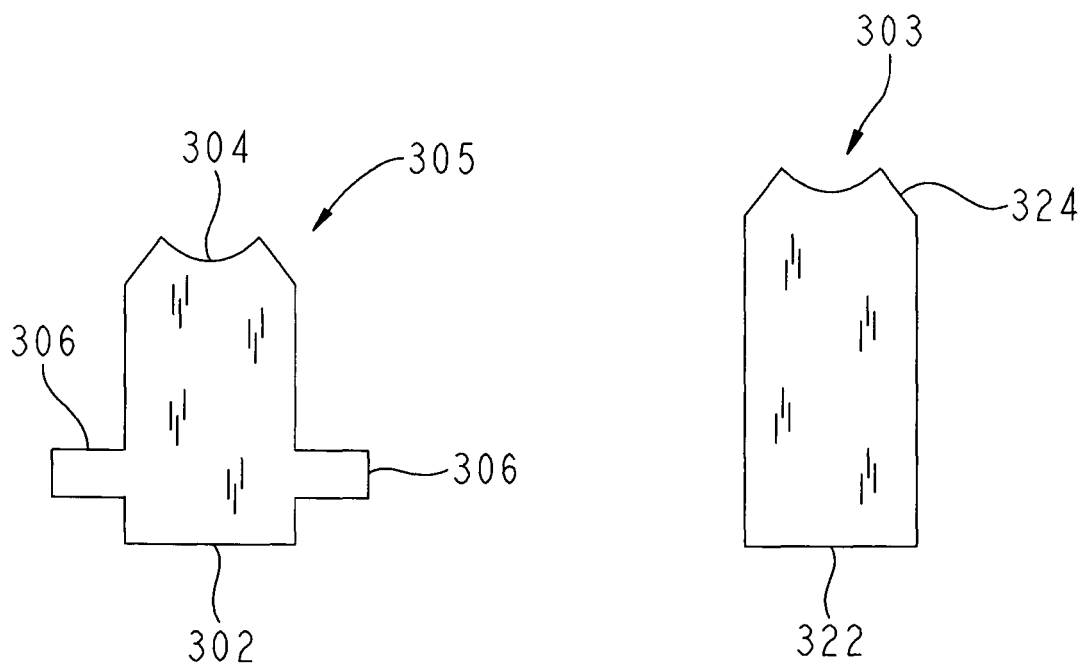
FIGS. 21 A-B are blown up perspective views of the top and bottom layers, respectively, of the test strip used in the panel sheer method.
Figure 21B:
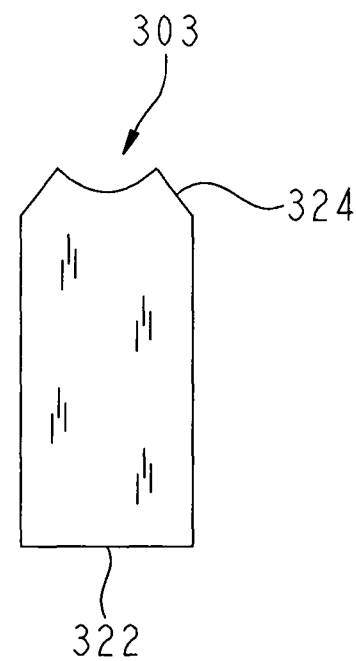

In a transmittance measurement, the analysis fluid 314 moves over the reagent 312 in the y-direction, shown by the axes in FIG. 21. A light source 318 emits a light beam along an optical path 316 that passes through an illuminated test field 315 of the reagent film 312 and strikes a light detector 320, such as a silicon photodiode. The photocurrent of the light detector 320 is converted to a proportional voltage, amplified and measured using conventional digitizing techniques in an output circuit 330. A rapid rate of data sampling (at least 10 measurements/sec) enables early reaction monitoring and kinetic measurement as required. In the preferred embodiment, the light source 318 is a narrow band LED driven by a digitally controlled, stable, temperature compensated current driver 332. The computations for the transmittance measurement are performed by a microprocessor 334. The microprocessor controls the current driver 332 and receives the output of the output circuit 330. The microprocessor 334 also receives the inputs from the buttons 128 and controls the output display 122.

Mass transfer in the z-direction into a reagent film 313 and measurement can be mathematically defined if the following conditions are met: (1) constant architecture of capillary channel system, (2) reproducible physical dimensions and chemical properties of rehydrated film 313 ('reagent film' being a homogeneous water-soluble polymer or rehydrated dispersion), (3) reproducible sample volume, (4) negligible variations in surface tension and viscosity of analysis fluid 314, e.g. whole blood, and (5) excess of reagent 312 (enzymes, chromogen) in the film 313. Under these conditions, a residence time for the analysis fluid 314 over the test zone 315 of the film 313 that is illuminated by the cross section of the photometric light beam 316 during measurement can be defined.

The designated planar dimensions of the cross section of the light beam 316 in the test field 315 are y [mm] in the direction of flow, and x [mm] perpendicular to the direction of flow. The capillary channel segment containing the analysis fluid 314 above the illuminated portion 315 of the film 313 has the dimensions x' perpendicular to the flow direction and perpendicular to the light path (width), y' in the flow direction (length), and z' perpendicular to the flow direction and parallel to the light path (height). Residence time ($\tau$) of the portion of the analytical sample 314 over the illuminated, measured volume fraction of the film 313 is Vp/v, where Vp is sample volume [mm$^3$], and v is rate of flow [mm/sec], which is equal to z'·x'·<dy/dt>, where z'·x' is the cross section of the capillary channel segment [mm$^2$] containing the analysis fluid 314 above the measured cross section of the film 313 (y·x) [mm$^2$], and <dy/dt> is the average rate of flow [mm/sec] of analysis fluid 314 across this channel segment (parabolic velocity profile). During the residence time of analysis fluid 314 above the test field 315 of the film 313, mass transfer into the reagent 312 in the film 313 occurs of an analyte component (i). The flux, $j_i$, of analyte component i perpendicular to the phase boundary (the surface of the film 313) is given by: $j_i=\beta \cdot (c_{i,b}-c_{i,g})$, where $j_i$=flux [mole/(sec·mm$^2$)], $\beta$=mass transfer coefficient [mm/sec], $c_{i,b}$=concentration of analyte i in the analysis fluid 314 [mole/mm$^3$], and $c_{i,g}$=concentration of analyte i at upper boundary of the film 313 [mole/mm$^3$]. Total amount, $a_i$, of analyte i transferred during residence time $\tau$ into the film 313 over the cross section y·x [mm$^2$] is: $a_i=j_i \cdot y \cdot x\tau=\beta \cdot y \cdot x \cdot \tau (c_{i,b}-c_{i,g})$. If $\beta$, y, x and $\tau$ are kept constant and $c_{i,g}$ is much smaller than $c_{i,b}$, then the equation simplifies to: $a_i=k \cdot c_{i,b}$, where k is constant ($k=\beta \cdot y \cdot x \cdot \tau$). This relationship is valid under above conditions (1) through (5), both in the case of diffusion controlled mass transfer (homogeneous swellable films), as well as in the case of interstitial bulk flow effected by capillary forces, superimposed by diffusion into rehydrating particles (layer of particles formed by drying of a dispersion).

If transferred analyte i ($a_i$) reacts quantitatively with the excess reagent 312 in the film 313, then absorbance A (measured on transparent films) at wavelengths characteristic for the reaction product of analyte i is linearly related to concentration (Lambert Beer's law): $A=\ln I_0/I=\epsilon \cdot c \cdot d=\epsilon \cdot a_i \cdot (x \cdot y)^{-1}$, where $I/I_0$=transmittance, $\epsilon$=molar extinction coefficient [mm$^2$/mole]. The derivations illustrate that measurements taken in absorbance mode solely depend on the mass of analyte i transferred across area x·y, and do not depend on distribution of analyte i over thickness dimension (z) of the film due to subsequent diffusion in the z-direction. This is in contrast to diffusion-dependent reflectance measurements taken on reactive surfaces. Thus, independence of signals from analyte and reaction product distribution in the z-direction makes absorbance or transmittance measurement intrinsically more precise than reflectance measurement.

The optics/electronics interface includes an optics module 336 that mates directly to a printed circuit board (PCB) 338, simplifying critical alignment of optics and test wand. The optics module 336 directs the collated light beam along the optical path 316 from the light source 318, through the test pad 315, to the detector 320. Tight tolerance molded parts for the interface between the test wand 200 and meter 10 will insure precise alignment of test field 315 and optical path 316. Complete insertion of the test strip end 202 of the consolidated test wand 200 is assured by an end-of-strip recognizing mechanical device, preferably a spring-driven snap-in pin.

A comprehensive serial interface 328 provides an output that can be connected for data transfer to a computer, allowing results to be sent to the doctor over a modem. This serial interface 328 also simplifies needed data retrieval during meter development, e.g. acquiring test data for calibration can be completely automated. Additionally the serial interface 328 can accommodate lot-code carrying media.

The meter 10 also includes a visual backup system to enable a user to confirm measurement results by the automated system, or to obtain results visually when the automated system is not operational, e.g., due to dead batteries. The visual backup system includes the visual back-up test wand opening 176, the color chart 136, the light pipe entrance aperture 134 on the back 13 of the meter 10, a light pipe exit aperture 178 in the visual back-up test wand opening 176, an exit aperture lens 180 and the light pipe 156 for transmitting light from the light pipe entrance aperture 134 to the light pipe exit aperture 178. The color chart 136 is a generally circular wheel having multiple sectors 135. Each sector 135 has a different shade of color such that the color chart 136 covers the spectrum of colors of the reacted test strips 204. Each sector 135 also has an aperture 137 located near the center of the sector 135. FIG. 3C shows a color wheel 136 with five sectors 135 of approximately seventy-two degrees of arc each. More sectors can be used to provide finer granularity on the visual backup reading, such as, for example, eight sectors that are each have forty-five degrees of arc. Alternatively, the color chart 136 could have a continuum of colors ranging across the spectrum of expected test results with apertures placed periodically around the continuum.

The following discussion will refer to the test strip 204 discussed above, however, the back up system works equally well with the test wand 200 regardless of the method of processing the analysis fluid 314, e.g., the panel separation method, the panel sheer method, the wiper method etc. The key is that the analysis fluid 314 has already reacted with the reagent 314 on the test strip before the test strip is inserted in the visual back-up test wand opening 176. The test strip end 202 of the consolidated test wand 200 and the visual back-up test wand opening 176 of the meter 10 are sized and shaped such that when the test strip end 202 with a reacted test strip 204 is fully inserted into the visual back-up test wand opening 176, the reaction area of the test strip 204 is visible through one of the apertures 137 in the color chart 136. Thus, the reacted area of the test strip 204 is visible through the aperture 137 and is surrounded by the color shade of the associated sector 135. To perform a visual backup, the user simply rotates the color chart 136 until the reacted area of the test strip 204 shows through the aperture 137 of the sector 135 with the color shade most closely matching the color shade of the reacted area of the test strip 204.

Applicant has investigated several different light path and light source options for illuminating the reacted area of the test strip 204 when fully inserted in the visual backup test wand opening 176 of the meter 10.

A first option is to not include the light pipe 156 and the light pipe apertures 134, 176, and simply to make the visual backup slot 176 on the rear 13 of the meter 10 under the color chart 136 a reflective white color. With this option, reflected light coming through the aperture 137 better illuminates the color shade of the reacted area of the test strip 204. The advantage of this option is that no external light or energy sources are necessary, and there is no opening to allow contaminants into the meter 10.

A second option is to have the light pipe 156 and the light pipe apertures 134, 176 without the exit aperture lens 180. With this option, light coming in through the light pipe opening 134 is reflected through the light pipe 156 to shine through the exit aperture 178, through the reacted area of the test strip 204, and through an aligned aperture 137 of the color chart 136. The advantage of this option is that no external light or energy sources are necessary, and the amount of light illuminating the test strip 204 is dependent on the size of the light pipe and not on the size of the apertures 137 of the color chart 136.

Another option is to have the light pipe 156 and the light pipe apertures 134, 176 with the exit aperture lens 180. With this option, light coming in through the light pipe opening 134 is reflected through the light pipe 156 to shine through the exit aperture lens 180, through the reacted area of the test strip 204, and through an aligned aperture 137 of the color chart 136. The advantage of this option is that no external light or energy sources are necessary, the amount of light illuminating the test strip 204 is dependent on the size of the light pipe and not on the size of the apertures 137 of the color chart 136, and there is no opening to allow contaminants into the meter 10.

Yet another option is to have a light source under the visual backup slot 176 on the rear 13 of the meter 10 under the color chart 136. With this option, light coming from the light source illuminates the color shade of the reacted area of the test strip 204. The advantage of this option is that it does not require a light pipe and the amount of light is not dependent on the size of the apertures 137 of the color chart 136. The disadvantage of this option is that it requires a light source which in turn requires additional energy.

Having described the invention in detail, it will be appreciated that variations and modifications can exist within the scope and spirit of the invention as defined by the appended claims.

We claim:

1. A body fluid testing system comprising a test wand and a meter, the meter having a test wand opening including a side wall to process an analysis fluid, said test wand comprising: a test strip having a proximal end and a distal end, said test strip containing a reagent and comprising a first layer having a first arm and a second, spaced layer defining a channel therebetween; said test strip being capable of receiving the analysis fluid at the distal end; and a test strip holder having a proximal end and a distal end; said test strip holder comprising a base and a slot, such that when said test strip is inserted in said test strip holder, said arm of said first layer extends through said slot of said test strip holder; said test strip holder being sized and shaped to be inserted in the test wand opening, the test wand opening and test strip being configured to engage each other to create a capillary gradient in the test strip for causing the fluid to flow in a proximal direction.

2. The body fluid testing system of claim 1 wherein the distal end has a surface to volume ratio, as said test wand is inserted into the test wand opening, the side wall of the test wand opening engages said first arm of said first layer, pulling said first arm and said first layer of said test strip in the proximal direction, to reduce the surface to volume ratio of the distal end, thereby increasing a capillary gradient, and thereby causing said analysis fluid to flow in the proximal direction to expose a portion of said reagent on said first layer that has reacted with the analysis fluid.

3. The body fluid testing system of claim 2, wherein said test strip holder further comprises a test strip retainer and a living hinge mechanism, said test strip retainer being connected to said base by said living hinge mechanism.

4. The body fluid testing system of claim 2, wherein said second layer comprises a second arm and a foot, said foot being located at the distal end of said test strip and said second arm being positioned to align with said first arm when said second layer is placed in the desired position above said first layer; and said test strip holder further comprises upstanding side walls along each side of said base between said proximal end and said distal end, the distal end of said side walls having a ramped surface; wherein, as said test wand is inserted into the test wand opening, the side wall of the test wand opening engages said first and second arms of said test strip, pulling said first and second arms and said first and second layers in the proximal direction, causing said foot of said second layer to engage said ramped surface of said side walls separating said second layer from said first layer, causing the analysis fluid to flow in the proximal direction to expose a portion of said reagent that has reacted with the analysis fluid.

5. The body fluid testing system of claim 4, wherein said test strip holder further comprises an optical path aperture, wherein, after said test wand is inserted in the test wand opening, the portion of said reagent that is above said optical path aperture has reacted with the analysis fluid.

6. The body fluid testing system of claim 2, wherein said second layer contains said reagent; wherein, as said test wand is inserted into the test wand opening, the side wall of the test wand opening engages said arm of said first layer of said test strip, pulling said first arm and said first layer in the proximal direction, causing the analysis fluid to flow in the proximal direction to expose a portion of said reagent that has reacted with the analysis fluid.

7. The body fluid testing system of claim 6, wherein said test strip holder further comprises an optical path aperture, wherein, after said test wand is inserted in the test wand opening, the portion of said reagent above said optical path aperture has reacted with the analysis fluid.

8. The body fluid testing system of claim 1 wherein the test wand opening engages the test strip to separate the first and the second layers to thereby cause the surface to volume ratio of the distal end to decrease relative to the proximal end.

9. The body fluid testing system of claim 1 wherein said second layer further comprises a second arm and a foot, wherein the first and second layers are separable, and wherein the separation of the first and second layers facilitates removal of the analysis fluid from the reagent.

10. The body fluid testing system of claim 1 wherein the distal end includes a surface to volume ratio, and wherein the test wand opening of the meter is configured for moving the distal end of the test want in a proximal direction to reduce the surface to volume ratio of the distal end, thereby increasing a capillary gradient for causing the analysis fluid to move in a proximal direction.

11. The body fluid testing system of claim 1 wherein as the test wand is inserted into the test wand opening of the meter, the side wall of the test wand opening engages the first arm of the first layer, pulling the first arm and the first layer of the test strip in a proximal direction, thereby causing the analysis fluid to flow in the proximal direction to expose a portion of the reagent on the first layer that has reacted with the analysis fluid.

12. A test wand for use with a meter having a test wand opening including a side wall to process an analysis fluid, said test wand comprising: a test strip having a proximal end and a distal end, said test strip containing a reagent and comprising a first layer having a first arm and a second layer spaced from the first and defining a channel therebetween; said test strip being capable of receiving the analysis fluid at the distal end; and a test strip holder having a proximal end and a distal end; said test strip holder comprising a base and a slot, such that when said test strip is inserted in said test strip holder, said arm of said first layer extends through said slot of said test strip holder; said test strip holder being sized and shaped to be inserted in the test wand opening, wherein, as said test wand is inserted into the test wand opening, the side wall of the test wand opening engages said first arm of said first layer, pulling said first arm and said first layer of said test strip in the proximal direction, causing said analysis fluid to flow in the proximal direction to expose a portion of said reagent on said first layer that has reacted with the analysis fluid, wherein said test strip holder further comprises a sample application pad and a wiper, said sample application pad being located on the distal side of said wiper; wherein, as said test wand is inserted into the test wand opening, the side wall of the test wand opening engages said first arm of said first layer, pulling said first arm and said first layer in the proximal direction, causing first layer to pass over said wiper of said test strip holder, wiping said analysis fluid from said first layer to expose a portion of said reagent that has reacted with the analysis fluid.

13. The test wand of claim 12, wherein said test strip holder further comprises an optical path aperture, wherein, after said test wand is inserted in the test wand opening, the portion of said reagent above said optical path aperture has reacted with the analysis fluid.

14. The test wand of claim 12, wherein said test strip holder further comprises a protrusion, wherein, when said test strip is inserted in said test strip holder, said protrusion exerts a force on said test strip causing said test strip to push against said wiper.

* * * * *